United States Patent
Senga et al.

(10) Patent No.: US 10,941,179 B2
(45) Date of Patent: Mar. 9, 2021

(54) METHOD FOR SUPPRESSING AGGREGATION OF POLYPEPTIDE

(71) Applicant: NATIONAL INSTITUTE OF ADVANCED INDUSTRIAL SCIENCE AND TECHNOLOGY, Tokyo (JP)

(72) Inventors: Yukako Senga, Ibaraki (JP); Hideki Watanabe, Ibaraki (JP); Shinya Honda, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 69 days.

(21) Appl. No.: 16/184,028

(22) Filed: Nov. 8, 2018

(65) Prior Publication Data
US 2019/0135860 A1 May 9, 2019

(30) Foreign Application Priority Data

Nov. 9, 2017 (JP) .............................. JP2017-216409

(51) Int. Cl.
| | |
|---|---|
| *C07K 1/22* | (2006.01) |
| *C07K 16/00* | (2006.01) |
| *C07K 1/14* | (2006.01) |
| *C07K 1/02* | (2006.01) |
| *C07K 14/00* | (2006.01) |
| *C07K 7/06* | (2006.01) |
| *C07K 7/08* | (2006.01) |
| *C07K 1/32* | (2006.01) |
| *C07K 16/06* | (2006.01) |
| *C07K 1/36* | (2006.01) |
| *A61K 39/395* | (2006.01) |

(52) U.S. Cl.
CPC .......... *C07K 1/32* (2013.01); *A61K 39/39591* (2013.01); *C07K 1/02* (2013.01); *C07K 1/145* (2013.01); *C07K 1/22* (2013.01); *C07K 1/36* (2013.01); *C07K 16/00* (2013.01); *C07K 16/065* (2013.01); *C07K 2319/30* (2013.01)

(58) Field of Classification Search
CPC . C07K 1/32; C07K 16/00; C07K 1/22; C07K 16/065; C07K 1/36; C07K 1/145; C07K 1/02; C07K 2319/30; C07K 14/001; C07K 7/08; C07K 7/06; C07K 14/00; A61K 39/39591
See application file for complete search history.

(56) References Cited

U.S. PATENT DOCUMENTS

| | | | |
|---|---|---|---|
| 8,372,950 B2 * | 2/2013 | Ito ............................ | C07K 1/22 530/326 |
| 9,382,297 B2 | 7/2016 | Honda et al. | |
| 2006/0205093 A1 * | 9/2006 | Prins ........................ | C07K 1/22 436/526 |
| 2007/0190047 A1 | 8/2007 | Brych et al. | |
| 2008/0064856 A1 | 3/2008 | Warne et al. | |
| 2014/0179898 A1 | 6/2014 | Honda et al. | |
| 2015/0353608 A1 * | 12/2015 | Watanabe ............ | C07K 14/001 530/324 |
| 2015/0377899 A1 | 12/2015 | Honda et al. | |

FOREIGN PATENT DOCUMENTS

| | | |
|---|---|---|
| JP | 2009-502972 A | 1/2009 |
| JP | 2009-530380 A | 8/2009 |
| JP | 2009-297018 A | 12/2009 |
| JP | 2010-081866 A | 4/2010 |
| JP | 2014-208669 A | 11/2014 |
| WO | 2012/165544 A1 | 12/2012 |
| WO | 2014/103203 A1 | 7/2014 |
| WO | 2014/115229 A1 | 7/2014 |

OTHER PUBLICATIONS

Burgess et al., Journal of Cell Biology vol. 111: pp. 2129-2138 (Year: 1990).*
Lazar et al., Molecular and Cellular Biology vol. 8: pp. 1247-1252 (Year: 1988).*
"Preclinical Development of Monoclonal Antibodies and Related Biologicals: Emerging Technologies and New Therapeutic Candidates," Business Insights Ltd., (2010) 18 pages total.
Nicole Casadevall, M.D. et al., "Pure Red-Cell Aplasia and Antierythropoietin Antibodies in Patients Treated with Recombinant Erythropoietin," The New England Journal of Medicine; Feb. 14, 2002; pp. 469-475; vol. 346, No. 7.
Sharon K. Gershon, Pharm.D. et al., "Pure Red-Cell Aplasia and Recombinant Erythropoietin," The New England Journal of Medicine; May 16, 2002; pp. 1584-1586; vol. 346, No. 20.
Amber Haynes Fradkin et al., "Immunogenicity of Aggregates of Recombinant Human Growth Hormone in Mouse Models," Journal of Pharmaceutical Sciences; Sep. 2009; pp. 3247-3264; vol. 98, No. 9.
John F. Carpenter et al., "Overlooking Subvisible Particles in Therapeutic Protein Products: Gaps that may Compromise Product Quality," J. Pharm Sci.; Apr. 2009; pp. 1201-1205; vol. 98, No. 4.

(Continued)

*Primary Examiner* — Phuong Huynh
(74) *Attorney, Agent, or Firm* — Sughrue Mion, PLLC

(57) ABSTRACT

The present invention relates to a method for suppressing aggregation of polypeptide. Specifically, the present invention relates to a method for suppressing, in a solution comprising an antibody or an Fc region-containing protein, formation of an aggregate derived from an antibody or an Fc region-containing protein having a non-native conformation, the method comprising: the steps of (i) binding an AF.2A1 polypeptide or an analog thereof with an aggregate derived from the antibody or Fc region-containing protein having a non-native conformation in the solution; and (ii) collecting the aggregate bound to the polypeptide or analog thereof from the solution.

9 Claims, 8 Drawing Sheets

Specification includes a Sequence Listing.

(56) References Cited

OTHER PUBLICATIONS

Suzanne Hermeling et al., "Antibody Response to Aggregated Human Interferon Alpha2b in Wild-type and Transgenic Immune Tolerant Mice Depends on Type and Level of Aggregation," Journal of Pharmaceutical Sciences; May 2006; pp. 1084-1096 vol. 95, No. 5.
John F. Carpenter et al., "Rational Design of Stable Protein Formulations: Theory and Practice," Pharmaceutical Biotechnology; 2002; pp. 109-133; vol. 13.
Xiaojun Zhao et al., "Designer short peptide surfactants stabilize G protein-coupled receptor bovine rhodopsin," PNAS; Nov. 21, 2006; pp. 17707-17712; vol. 103, No. 47.
Aki Nagai et al., "Dynamic Behaviors of Lipid-Like Self-Assembling Peptide $A_6D$ and $A_6K$ Nanotubes," Journal of Nanoscience and Nanotechnology; 2007; pp. 2246-2252; vol. 7.
Peter M. Bowers et al., "Mammalian cell display for the discovery and optimization of antibody therapeutics," Methods; 2014; pp. 44-56; vol. 65.
Michael W. Handlogten et al., "Intracellular response to process optimization and impact on productivity and product aggregates for a high-titer CHO cell process," Biotechnology and Bioengineering; 2017; pp. 126-138; vol. 115.
Sunny C.H. Yueh et al., "An improved method for haptoglobin 1-1, 2-1, and 2-2 purification using monoclonal antibody affinity chromatography in the presence of sodium dodecyl sulfate," Journal of Chromatography B; 2007; pp. 210-217; vol. 845.
Hiroshi Imamura et al., "Kinetics of Antibody Aggregation at Neutral pH and Ambient Temperatures Triggered by Temporal Exposure to Acid," The Journal of Physical Chemistry B; 2016; pp. 9581-9589; vol. 120.
Hiroshi Imamura et al., "Fate of a Stressed Therapeutic Antibody Tracked by Fluorescence Correlation Spectroscopy: Folded Monomers Survive Aggregation," The Journal of Physical Chemistry B; 2017; pp. 8085-8093; vol. 121.
Mary E.M. Cromwell et al., "Protein Aggregation and Bioprocessing," The AAPS Journal; 2006; pp. E572-E579; vol. 8, No. 3, Article 66.
Karin Welfle et al., "Conformation, pH-induced conformational changes, and thermal unfolding of anti-p24 (HIV-1) monoclonal antibody CB4-1 and its Fab and Fc fragments," Biochimica et Biophysica Acta; 1999; pp. 120-131; vol. 1431.
Michael J.W. Thies et al., "The Alternatively Folded State of the Antibody $C_H3$ Domain," Journal of Molecular Biology; 2001; pp. 1077-1085; vol. 309.
Laszlo Várady et al., "Rapid High-Performance Affinity Chromatography on Micropellicular Sorbents," Journal of Chromatography; 1988; pp. 207-215; vol. 458.
Hideki Watanabe et al., "Optimizing pH Response of Affinity between Protein G and IgG Fc," The Journal of Biological Chemistry; May 1, 2009; pp. 12373-12383; vol. 284, No. 18.
Hideki Watanabe et al., "Structure-based histidine substitution for optimizing pH-sensitive *Staphylococcus* protein A," Journal of Chromatography B; 2013; pp. 155-160; vol. 929.
Masayuki Tsukamoto et al., "Engineered protein A ligands, derived from a histidine-scanning library, facilitate the affinity purification of IgG under mild acidic conditions," Journal of Biological Engineering; 2014; pp. 1-9; vol. 8, No. 15.
Susanne Gülich et al., "Protein engineering of an IgG-binding domain allows milder elution conditions during affinity chromatography," Journal of Biotechnology; 2000; pp. 233-244; vol. 76.
Rongxiu Li et al., "Design, synthesis, and application of a Protein A mimetic," Nature Biotechnology; Feb. 1998; vol. 16; pp. 190-195.
Tsutomu Arakawa et al., "Elution of antibodies from a Protein-A column by aqueous arginine solutions," Protein Expression & Purification; 2004; pp. 244-248; vol. 36.
Tsumoto et al., "Review: Why is Arginine Effective in Suppressing Aggregation?" Protein & Peptide Letters; 2005; pp. 613-619; vol. 12.
Tsutomu Arakawa et al., "The effects of arginine on protein binding and elution in hydrophobic interaction and ion-exchange chromatography," Protein Expression & Purification; 2007; vol. 54; pp. 110-116.
Daisuke Ejima et al., "Arginine as an effective additive in gel permeation chromatography," Journal of Chromatography A; 2005; pp. 49-55; vol. 1094.
Linda O. Narhi et al., "Classification of Protein Aggregates," Journal of Pharmaceutical Sciences; Feb. 2012; pp. 493-498 vol. 101, No. 2.
William F. Weiss IV et al., "Nonnative Protein Polymers: Structure, Morphology, and Relation to Nucleation and Growth," Biophysical Journal; Dec. 2007 pp. 4392-4403.; vol. 93.
Marisa K. Joubert et al., "Classification and Characterization of Therapeutic Antibody Aggregate," The Journal of Biological Chemistry; Jul. 15, 2011; pp. 25118-25133; vol. 286, No. 28.
Hideki Watanabe et al., "Tracing Primordial Protein Evolution through Structurally Guided Stepwise Segment Elongation," The Journal of Biological Chemistry; Feb. 7, 2014; pp. 3394-3404; vol. 289, No. 6.
Yukako Senga et al., "AlphaScreen-based homogeneous assay using a pair of 25-residue artificial proteins for high-throughput analysis of non-native IgG," Scientific Reports; Sep. 29, 2017; pp. 1-12; vol. 7, No. 12466.

* cited by examiner

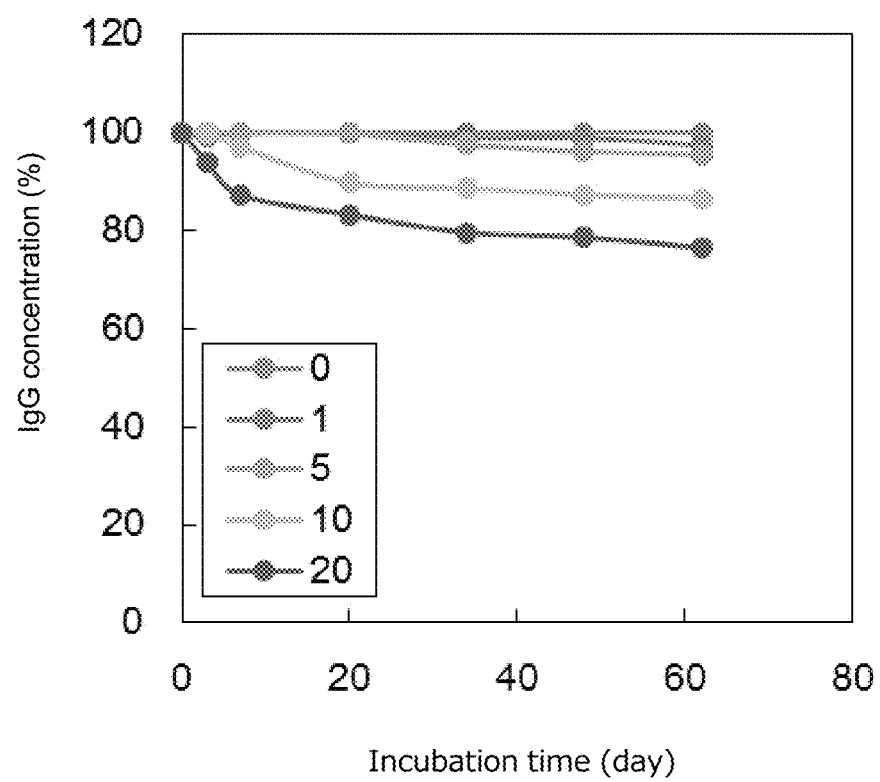
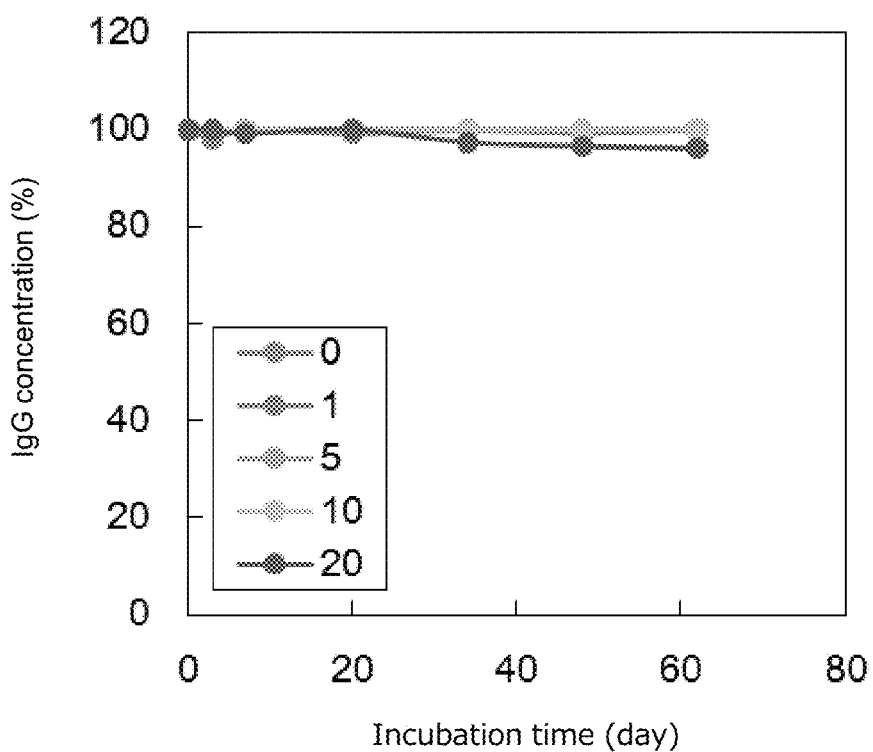

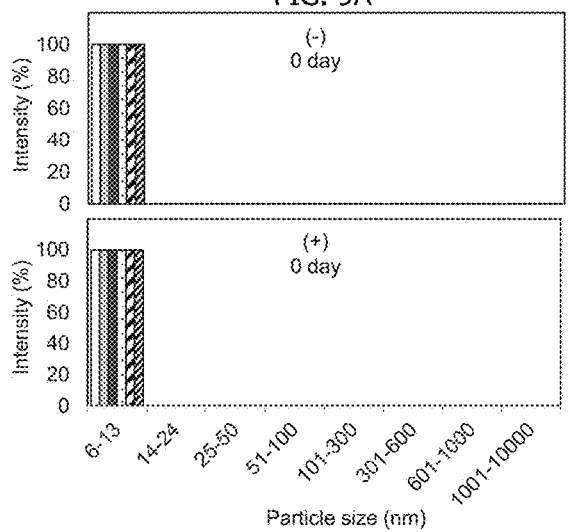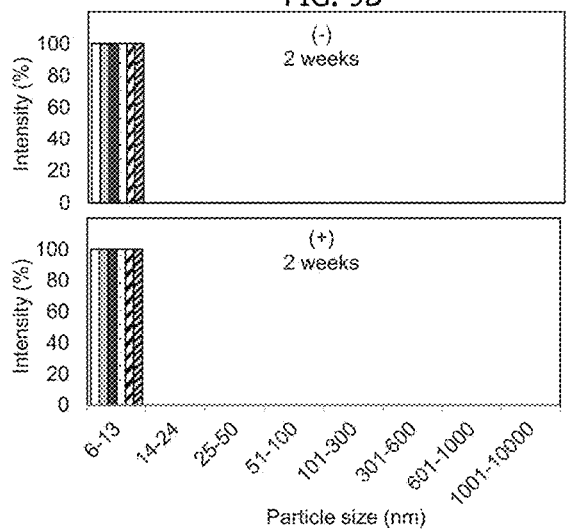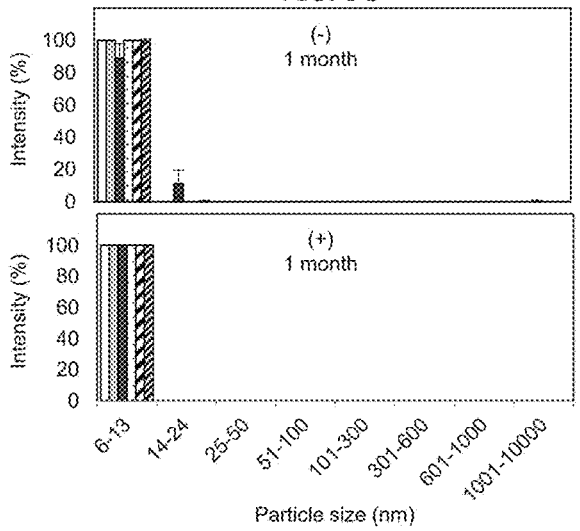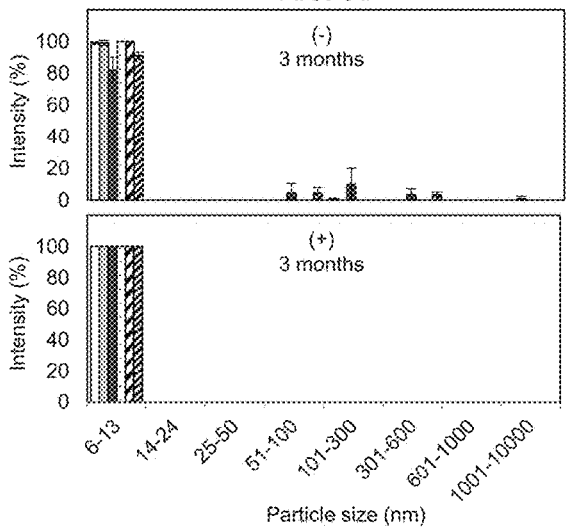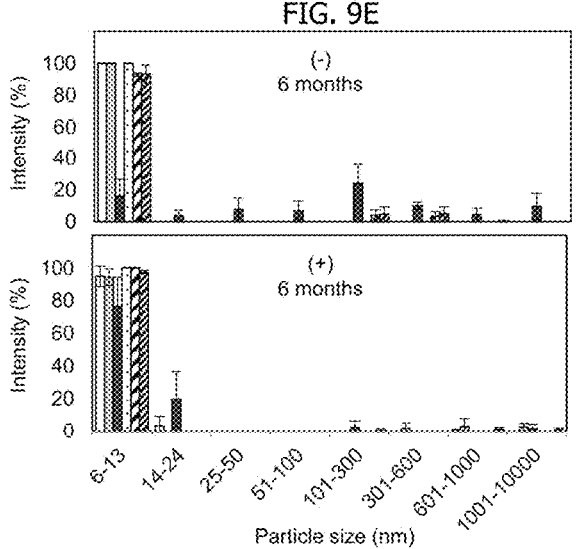

METHOD FOR SUPPRESSING AGGREGATION OF POLYPEPTIDE

CROSS-REFERENCE TO RELATED APPLICATION

The present application claims priority to Japanese Patent Application No. 2017-216409 (filed on Nov. 9, 2017), the contents of which are herein incorporated by reference.

BACKGROUND OF THE INVENTION

Field of the Invention

The present invention relates to a method for suppressing aggregation of polypeptide.

Description of the Related Art

So-called antibody drug, which makes use of monoclonal antibodies in the therapeutic application and annual sales of which exceed 30 billion dollars, is the largest segment in biopharmaceuticals and also the fastest growing segment in the whole pharmaceutical industry. 23 full-size monoclonal antibodies and three monoclonal antibody fragments have been marketed so far and some of them have already become blockbusters whose annual sales exceed 1 billion dollars. Between 1995 and 2007, the number of drug candidate monoclonal antibodies entering clinical trials increased three or more times and the number further continues increasing ("Preclinical Development of Monoclonal Antibodies and Related Biologicals: Emerging technologies and new therapeutic candidates" (2010)[1]).

Antibody drugs are required to be formulations that can stably be stored over a long period of time. Antibody drugs, which are protein origin, have concerns on their immunogenicity from the viewpoint of efficacy and safety. Actually, some antibody drugs that had been confirmed on their safety caused adverse events due to the induction by their immunogenicity and use of them were stopped (Casadevall (2002)[2]; Gershon (2002)[3]). The immunogenicity of an antibody drug means that antibodies are produced against the antibody drug. Factors that influence the immunogenicity include those derived from components from products and the manufacturing process and those derived from the immune response of the individual patient. Those derived from components from products and the manufacturing process include the primary structure, modification, and structure of the antibody, host cell proteins (HCPs), aggregates of the antibody, addition of non-human sugar chain, properties of additives and containers, and the like. Those derived from the immune response of the individual patient include the health status of the patient, the route of administration, the dose and the duration of administration, genetic factors, and the like. These factors cause not only the reduction of the therapeutic effect on the patient, but also anaphylaxis and cytokine release syndrome, and crossreaction with endogenous protein. As a result, the immunogenicity leads to severe adverse events.

In recent years, increasing findings implicate aggregates of antibodies, which is one of the risk factors of the immunogenicity, with the immunogenicity (Fradkin (2009)[4]; Carpenter (2009)[5]; Hermeling (2006)[6]). Since antibody drugs are preparations of protein origin, their properties are largely dependent on the manufacturing process. Actually, the possibility of structural change of such antibodies by a variety of stress that occurs to the antibodies during culture and purification process has been suggested. Moreover, antibody drugs are desired to be stored stably for a long period of time while they are at high concentrations. Antibody drugs at high concentrations are difficult to be maintained stable in aqueous solutions and aggregate due to the change in structure from their native conformation or the association by environmental stress during the storage. Therefore, when aggregates of antibody drugs, which are known to have the advantage of less side effects, are associated with side effects, it is considered to be essential to take measures to remove them as much as possible and/or to have improvement in the technology of analysis. The technology for suppressing aggregation of protein in general will be described below.

In the current technology of aggregation suppression, aggregation is suppressed by adding a denaturing agent such as urea or a particular amino acid(s) to aqueous protein solutions. Furthermore, surfactants that weakly interact with protein, such as Tween80 or TritonX-100, are used as means for improving the solubility of protein. However, the existing technology has problems such as denature of protein structure and inhibition of activity. There are many proteins that may become therapeutic agents for many diseases, but it is not easy to formulate such a protein while maintaining its pharmacological effect in the development of protein pharmaceutical preparations. A sugar or a sugar alcohol may be added to formulations for the purpose of increasing structural stability of protein (Carpenter (2002)[7]). An inhibitor for aggregation of a protein (JP2014-208669A), formulations that inhibit protein aggregation (JP2009-502972T), and methods for reducing protein aggregation (JP2009-530380T) will be introduced below.

JP2014-208669A discloses a technique for suppressing protein aggregation by lowering the viscosity of a protein solution using a peptidic surfactant AAAAAAD or AAAAAAK to suppress protein aggregation during the formulation for the purpose of medical application of proteins containing an antibody. The peptidic surfactants to be used are known to have the effect of stabilizing membrane proteins such as G protein-coupled receptor bovine rhodopsin and the property of self-assembling (Zhao (2006)[8]; Nagai (2007)[9]), but the use as a suppressor of protein aggregation had been unknown before JP2014-208669A.

JP2009-502972T discloses an invention of formulations that inhibit protein aggregate formation induced by one or more freeze/thaw cycles and stirring, comprising an inhibitor of insoluble aggregate formation in predetermined buffer conditions. Specifically, the amount of aggregates is reduced by contacting a solution comprising a protein or protein fragment with an amount of an inhibitor of insoluble aggregate formation effective to inhibit insoluble aggregate formulation. The buffer conditions are those of a phosphate buffer having a pH range of about 4.0 to about 8.0. The inhibitor includes $MgCl_2$, propylene glycol, Pluronic-F68, Poloxamer 188, ethanol, or a combination thereof.

JP2009-530380T discloses methods for reducing protein aggregation involving adding methionine to a formulation (comprising a surfactant and any of citric acid, succinic acid, histidine, and tris buffer) to a concentration of about 0.5 mM to about 145 mM. It is shown that protein aggregation is reduced in such a formulation in comparison with that in a formulation lacking methionine.

For antibody drugs, efforts to reduce the formation of aggregates, other than the approaches described above, including the optimization of antibody-producing cell lines and media, studies on buffer solutions and additives in antibody solutions and purification conditions, and elucidation of the mechanism of aggregate formation are in progress (Bowers (2014)[10]; Handlogten (2017)[11]; Yueh (2007) [12]; Imamura (2016)[13]; Imamura (2017)[14]). However, there is still the risk of adverse events due to aggregation. Some precedent studies indicate that aggregation reaction evolves over time. Therefore, if there are aggregates in an antibody solution, then it is considered that there is a risk that immunogenicity is induced by the formation of large aggregates during the storage. Therefore, it is ideal to remove aggregates from antibody solutions just before administration of the solutions.

The aggregation of an antibody is considered to occur during the production process, the purification process, and the storage of the antibody (Cromwell (2006)[15]). In particular, the purification of antibodies involves a pH change to very low pH in conditions for the elution from Protein A and this is associated with the risk of conformational change and aggregation of antibodies (Welfle (1999)[16]; Thies (2001)[17]). Therefore, various approaches to removing aggregates during the production and purification processes have been tried. Examples of such approaches include methods involving change the conditions for the antibody extraction to relatively mild ones (U.S. Pat. No. 9,382,297B, JP2009-297018A, WO 2012/165544, JP2010-081866A; Varady (1988)[18]; Watanabe (2009)[19]; Watanabe (2013)[20]; Tsukamoto (2014)[21], use of Low affinity matrix (Gulick (2000)[22]; Li (1998)[23]), and techniques involving addition of arginine for suppressing aggregation (Arakawa (2004)[24]; Tsumoto (2005)[25]; Arakawa (2007) 26); Ejima (2005)[22]).

There are various steps in a production process for removing antibody aggregates. Generally, monoclonal antibodies are produced by cell culturing of cell lines derived from animals. In usual operations for purifying an antibody from a liquid cell culture, the liquid cell culture is centrifuged and suspended components are first precipitated and removed. Then, cell debris having a size of 1 μm or less, which cannot be eliminated by centrifugation, is removed by size filtration with a microfiltration membrane. Furthermore, sterile filtration with a filtration membrane having a maximum pore size of 0.22 μm or less is conducted for sterilization to obtain a sterile solution containing the protein of interest (harvest step). Subsequently, also contaminates such as host cell protein (HCP), deoxyribonucleic acid (DNA), endotoxin, virus, and protein A released from the column, but not only the aggregates of the antibody, are removed from this sterile solution using a purification process with a combination of plural chromatographic techniques, represented by the affinity chromatography using protein A to separate and purify the protein of interest (downstream step). The purity of a protein is increased through plural purification processes but it is difficult to separate and remove non-native conformational forms of the protein and assemblies of the protein. Moreover, aggregates are usually removed by filtration with a filtration membrane having a pore size of 0.22 μm or less or a method of removal employing plural types of chromatography in current production processes and there are size ranges of aggregates that cannot be removed.

There are a wide variety of aggregates from oligomers to visible particles. The reasons for such a variety include sizes and forms of stress-induced aggregates that vary depending on the environmental stress. These aggregates are classified into <100 nm, 100 to 1000 nm (submicrometer), 1 to 100 μm, >100 μm by the classification by Narhi (Narhi (2012) [28]). Such aggregates that are difficult to be removed by existing methods are aggregates in the ranges of <100 nm and 100 to 220 nm, which is a part of the submicrometer range.

Based on plural precedent studies, small aggregates are considered to be likely to form larger aggregates (Weiss (2007)[29]; Joubert (2011)[30]). Therefore, even if a protein preparation of a high purity is obtained through a production process, the presence of small sizes of aggregates is considered to result in the induction of larger aggregates during the storage for a long period of time. Thus, it is important to evaluate the rate of aggregate formation in antibody solutions after the removal of sizes of aggregates that cannot be removed by any existing technique by employing one of the artificial proteins and probes that specifically interacts with aggregates having a size of 220 nm or less, which are difficult to be removed or prevented from the formation by existing techniques.

The present inventors made an artificial protein AF.2A1 having 25 residues and exhibiting an affinity to the Fc region of human IgG using the 10-residue microprotein chignolin and an artificial protein library (WO 2014/103203) containing randomized amino acid sequences (Watanabe (2014)[31]). AF.2A1 exhibits specific high affinity to the Fc region in a non-native structure generated by acid treatment, heat-treatment, reduction, or the like and a technique that can strictly distinguish a non-native conformational from and a native conformational form of the Fc region was developed (WO 2014/115229).

CITATION LIST

1) "Preclinical Development of Monoclonal Antibodies and Related Biologicals: Emerging technologies and new therapeutic candidates", pp. 16-20. Business Insights Ltd.
2) Casadevall, N., Nataf, J., Viron, B., Kolta, A., Kiladjian, J. J., Martin-Dupont, P., Michaud, P., Papo, T., Ugo, V., Teyssandier, I., Varet, B., and Mayeux, P. (2002) N. Engl. J. Med. 346, 469-475
3) Gershon, S. K., Luksenburg, H., Cote, T. R., and Braun, M. M. (2002) N. Engl. J. Med. 346, 1584-1586
4) Fradkin, A. H., Carpenter, J. F., and Randolph, T. W. (2009) J Pharm Sci 98, 3247-3264
5) Carpenter, J. F., Randolph, T. W., Jiskoot, W., Crommelin, D. J., Midaugh, C. R., Winter, G., Fan, Y. X., Kirshner, S., Verthelyi, D., Kozlowski, S., Clouse, K. A., Swann, P. G., Rosenberg, A., and Cherney, B. (2009) J Pharm Sci 98, 1201-1205
6) Hermeling, S., Schellekens, H., Maas, C., Gebbink, M. F., Crommelin, D. J., and Jiskoot, W. (2006) J Pharm Sci 95, 1084-1096
7) Carpenter, J. F., Chang, B. S., Garzon-Rodriguez, W. and Randolph, T. W. (2002) Pharm Biotechnol 13, 109-133
8) Zhao, X., Nagai, Y., Reeves, P. J., Kiley, P., Khorana, H. G., and Zhang, S. (2006) PNAS 103, 17707-17712
9) Nagai, A., Nagai, Y., Qu, H., and Zhang, S. (2007) J. Nanosci. Nanotechnol. 7, 2246-2252
10) Bowers, P. M., Horlick, R. A., Kehry, M. R., Neben, T. Y., Tomlinson, G. L., Altobell, L., Zhang, X., Macomber, J. L., Krapf, I. P., Wu, B. F., McConnell, A. D., Chau, B., Berkebile, A. D, Hare, E., Verdino, P., and King, D. J. (2014) Methods 65, 44-56
11) Handlogten, M. W., Lee-O'Brien, A., Roy, G., Levitskaya, S. V., Venkat, R., Singh, S., and Ahuja, S. (2017) Biotechnol. Bioeng.
12) Yueh, S. C., Lai, Y. A., Chen, W. L., Hsu, H. H., and Mao, S. J. (2007) Biotechnol. Bioeng. 845, 210-217

13) Imamura, H., and Honda, S. (2016) J. Phys. Chem. B 120, 9581-9589
14) Imamura, H., Sasaki, A., and Honda, S. (2017) J. Phys. Chem. B 121, 8085-8093
15) Cromwell, M. E., Hilario, E., and Jacobson, F. (2006) AAPS J 8, E572-579
16) Welfle, K., Misselwitz, R., Hausdorf, G., Hohne, W., and Welfle, H. (1999) Biochim Biophys Acta 1431, 120-131
17) Thies, M. J., Kammermeier, R., Richter, K., and Buchner, J. (2001) J Mol Biol 309, 1077-1085
18) Varady, L., Kalghatgi, K., and Horvath, C. (1988) J Chromatogr 458, 207-215
19) Watanabe, H., Matsumaru, H., Ooishi, A., Feng, Y., Odahara, T., Suto, K., and Honda, S. (2010) J. Biol. Chem. 284, 12373-12383
20) Watanabe, H., Matsumaru, H., Ooishi, A., and Honda, S. (2013) Chromatogr. B Analyt. Technol. Biomed. Life Sci. 929, 155-160
21) Tsukamoto, M., Watanabe, H., Ooishi, A., and Honda, S. (2014) J. Biol. Eng. 8, 15
22) Gulich, S., Uhlen, M., and Hober, S. (2000) J Biotechnol 76, 233-244
23) Li, R., Dowd, V., Stewart, D. J., Burton, S. J., and Lowe, C. R. (1998) Nat Biotechnol 16, 190-195
24) Arakawa, T., Philo, J. S., Tsumoto, K., Yumioka, R., and Ejima, D. (2004) Protein Expr Purif 36, 244-248
25) Tsumoto, K., Ejima, D., Kita, Y., and Arakawa, T. (2005) Protein Pept Lett 12, 613-619
26) Arakawa, T., Tsumoto, K., Nagase, K., and Ejima, D. (2007) Protein Expr Purif 54, 110-116
27) Ejima, D., Yumioka, R., Arakawa, T., and Tsumoto, K. (2005) J. Chromatogr. A 1094, 49-55
28) Narhi, L. O., Schmit, J., Bechtold-Peters, K., and Sharma, D. (2012) J. Pharm. Sci. 101, 493-498
29) Weiss, W. F. 4th., Hodgdon, T. K., Kaler, E. W., Lenhoff, A. M. and Roberts, C. J. (2007) Biophys J. 93, 4392-4403
30) Joubert, M. K., Luo, Q., Nashed-Samuel, Y., Wypych, J. and Narhi, L. O. (2011) J Biol Chem. 286, 25118-25133
31) Watanabe H, Yamasaki K, Honda S. (2014) J Biol Chem. 289, 3394-3404

SUMMARY OF THE INVENTION

An object of the present invention is to provide a method for suppressing formation of an aggregate in a solution comprising a native form antibody.

The present inventors paid their attention to the artificial protein AF.2A1 that can strictly distinguish a non-native conformational form of the Fc region of human IgG as means to achieve the aforementioned object. It is inferred that this artificial protein can bind to monomers to aggregates of non-native conformation antibodies. However, it was unknown how large are the aggregates derived from an antibody having non-native conformation that AF.2A1 can bind to and whether it has the binding that can tolerate the removal treatment of the aggregates. Therefore, the present inventors investigated the suppressing effect of the AF.2A1 peptide on the formation of such aggregates. As a result, the present inventors have found that aggregates including those having a size of 0.22 um or less, which cannot be removed by existing techniques, can be removed by immunoprecipitation using the AF.2A1 peptide and magnetic beads. Accordingly, the present inventors have found that the AF.2A1 peptide has the binding sufficiently applicable to treatments for removing aggregates in combination with a known technique. As used herein, monomers of non-native conformation antibodies and small aggregates having a size of 220 nm or less are defined as "aggregation precursors". The present inventors have also found that the aggregate formation that could occur latter can be suppressed by removing these aggregation precursors using the AF.2A1 peptide. The present invention was completed by these findings and includes the following aspects.

One aspect of the present invention relates to (1) a method for suppressing, in a solution comprising an antibody or an Fc region-containing protein, formation of an aggregate derived from an antibody or an Fc region-containing protein having a non-native conformation, the method comprising: the steps of (i) binding an AF.2A1 polypeptide or an analog thereof with a monomer and an aggregate derived from the antibody or Fc region-containing protein having a non-native conformation in the solution; and (ii) collecting the monomer and aggregate bound to the polypeptide or analog thereof from the solution.

Here, the method for suppressing formation of an aggregate according to the present invention is, in one embodiment, (2) the method according to (1) above, wherein the aggregate comprises an aggregate precursor having a particle size less than 0.22 μm.

Moreover, the method for suppressing formation of an aggregate according to the present invention is, in one embodiment, (3) the method according to (1) or (2) above, wherein the aggregate comprises an aggregate having a size equal to or larger than that of a dimer.

Moreover, the method for suppressing formation of an aggregate according to the present invention is, in one embodiment, (4) the method according to any of (1) to (3) above, wherein the AF.2A1 polypeptide or analog thereof consists of an amino acid sequence set forth in (A) or (B) below:

(A) the amino acid sequence set forth in SEQ ID NO: 1; or (B) an amino acid sequence modified from the amino acid sequence set forth in SEQ ID NO: 1 by substitution, addition, or deletion of one or several amino acids, wherein the polypeptide consisting of the amino acid sequence exhibits binding activity to an aggregate comprising an antibody or an Fc region-containing protein having a non-native conformation.

Moreover, the method for suppressing formation of an aggregate according to the present invention is, in one embodiment, (5) the method according to (4) above, wherein the AF.2A1 polypeptide or analog thereof consists of an amino acid sequence set forth in any of SEQ ID NOs: 1 and 3 to 25.

Moreover, the method for suppressing formation of an aggregate according to the present invention is, in one embodiment, (6) the method according to any of (1) to (5) above, wherein the antibody or Fc region-containing protein having a non-native conformation has a non-native conformation caused by stress selected from the group consisting of acid treatment, heating, reduction, oxidization, freeze-thawing, and a physical stimulation.

Moreover, the method for suppressing formation of an aggregate according to the present invention is, in one embodiment, (7) the method according to any of (1) to (6) above, wherein the antibody is human immunoglobulin G1 to 4.

Moreover, the method for suppressing formation of an aggregate according to the present invention is, in one embodiment, (8) the method according to any of (1) to (7) above, wherein the antibody is a human antibody, a chimeric antibody, a humanized antibody, or a murine antibody. Moreover, the method for suppressing formation of an aggregate according to the present invention is, in one embodiment, (9) the method according to any of (1) to (8) above, wherein the AF.2A1 polypeptide or analog thereof is immobilized onto a solid-phase carrier.

Moreover, the method to suppress the formation of the aggregate of the present invention in one embodiment,

(10) the method according to (9) above, wherein the solid-phase carrier is a particle having a particle size of 1 to 10 µm.

Moreover, the method for suppressing formation of an aggregate according to the present invention is, in one embodiment,

(11) the method according to (9) or (10) above, wherein the solid-phase carrier is a magnetic particle or a porous particle made of a polymer resin.

Moreover, the method for suppressing formation of an aggregate according to the present invention is, in one embodiment,

(12) the method according to any of (8) to (10) above, wherein the AF.2A1 polypeptide or analog thereof is immobilized onto a solid-phase carrier via any binding selected from the group consisting of biotin-avidin, biotin-streptavidin, and biotin-neutravidin.

Moreover, the present invention relates to, in another aspect,

(13) a method of producing an antibody, comprising the method for suppressing formation of an aggregate derived from an antibody or an Fc region-containing protein having a non-native conformation according to (1) above.

Moreover, the present invention relates to, in another aspect,

(14) a method of producing an antibody drug, comprising the method for suppressing formation of an aggregate derived from an antibody or an Fc region-containing protein having a non-native conformation according to (1) above.

Moreover, the present invention relates to, in another aspect,

(15) an aggregate formation suppressor for suppressing formation of an aggregate in a solution comprising an antibody or an Fc region-containing protein, comprising a solid-phase carrier onto which an AF.2A1 polypeptide or an analog thereof consisting of an amino acid sequence set forth in (A) or (B) below is immobilized, wherein the solid-phase carrier is a particle having a particle size of 1 to 10 µm:

(A) an amino acid sequence set forth in SEQ ID NO: 1, or
(B) an amino acid sequence modified from the amino acid sequence set forth in SEQ ID NO: 1 by substitution, addition, or deletion of one or several amino acids, wherein the polypeptide consisting of the amino acid sequence has a function of binding to an aggregate comprising an antibody or an Fc region-containing protein having a non-native conformation.

Moreover, the aggregate formation suppressor according to the present invention is, in one embodiment, (16) the aggregate formation suppressor according to (15) above, wherein the AF.2A1 polypeptide or analog thereof consists of an amino acid sequence set forth in any of SEQ ID NOs: 1 and 3 to 25.

Moreover, the aggregate formation suppressor according to the present invention is, in one embodiment, (17) the aggregate formation suppressor according to (15) or (16) above, wherein the solid-phase carrier is a magnetic particle or a porous particle made of a polymer resin.

Moreover, the aggregate formation suppressor according to the present invention is, in one embodiment, (18) the aggregate formation suppressor according to any of (15) to (17) above, wherein the AF.2A1 polypeptide or analog is immobilized onto a solid-phase carrier via any binding selected from the group consisting of biotin-avidin, biotin-streptavidin, and biotin-neutravidin.

Advantageous Effects of Invention

According to the method for suppressing formation of an aggregate according to the present invention, the aggregate formation that may occur later in an antibody solution containing non-native monomer antibodies that are difficult to measure with an existing apparatus and small aggregates that are difficult to remove by an existing technique can be suppressed. This makes it possible to maintain the bioactivity of antibodies for a long period of time and to elongate the storage life of protein formulations containing an antibody.

BRIEF DESCRIPTION OF THE DRAWINGS

FIG. 6A is a graph illustrating the result of measurement of the mass of protein contained in the soluble fraction obtained by mixing a native antibody and 0 to 20% of an acid-stressed antibody but not subjecting the mixture to the removal operation with AF.2A1 beads; FIG. 6B is a graph illustrating the result of measurement of the mass of protein contained in the soluble fraction obtained by mixing a native antibody and 0 to 20% of an acid-stressed antibody and subjecting the mixture to the removal operation with AF.2A1 beads.

(FIG. 8E, pH 4; FIG. 8F) to a native antibody and subjecting the stressed antibody to a treatment for suppressing formation of aggregates with AF.2A1 beads, in which the white and gray bars respectively indicate the results of the measurements with or without the treatment for suppressing formation of aggregates with AF.2A1 beads;

FIGS. 9A to 9E are graphs illustrating the results of DLS measurement of a particle size when monoclonal antibodies (mAb4, mAb5) were treated with AF.2A1 beads and left to stand at a temperature of 4 degrees Celsius, 25 degrees Celsius, or 37 degrees Celsius for 0 days to 6 months. The upper graphs in FIGS. 9A to 9E illustrate the results of measurement without the treatment for suppressing formation of aggregates and the lower graphs in FIGS. 9A to 9E illustrate the results of measurement with the treatment.

DETAILED DESCRIPTION OF THE PREFERRED EMBODIMENTS

Figure 1:
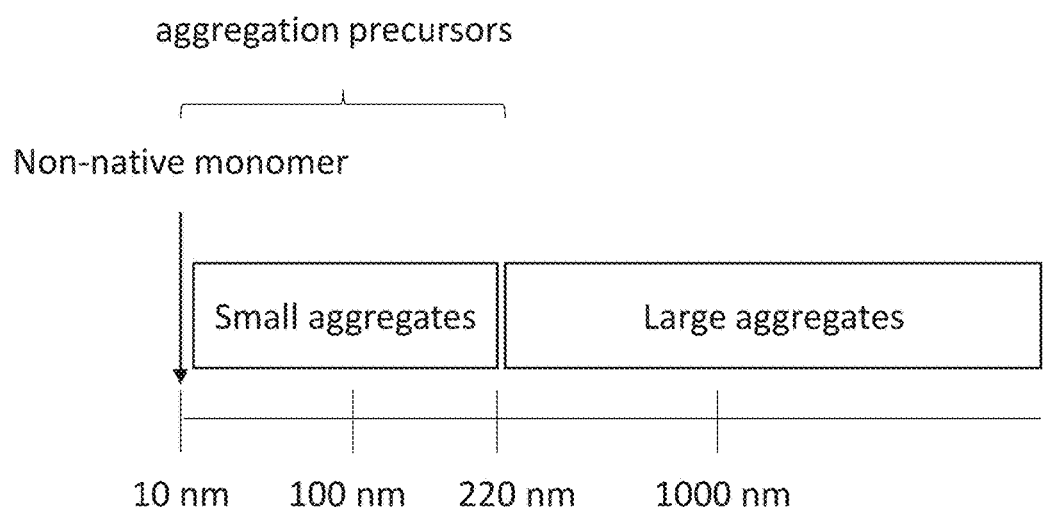
FIG. 1 illustrates a definition of aggregates used herein, in which aggregate precursors are defined to be small aggregates that cannot be removed by the existing technology (0.22 um filter) and non-native monomers.

One aspect of the present invention relates to a method for suppressing, in a solution comprising an antibody or an Fc region-containing protein, formation of an aggregate derived from an antibody or an Fc region-containing protein having a non-native conformation.

The method for suppression comprises the steps of:
(i) binding an AF.2A1 polypeptide or an analog thereof with a monomer and an aggregate derived from the antibody or Fc region-containing protein having a non-native conformation in the solution;
(ii) collecting the monomer and aggregate bound to the polypeptide or analog thereof from the solution.

As used herein, the "antibody" refers to an antibody having an Fc region wherein a non-native conformation is generated in the Fc region in stress environments. The antibody is not limited, as long as it is such an antibody as described above, to a human native antibody and examples thereof include chimeric antibodies, humanized antibodies, recombinant antibodies such as murine antibodies, fragmented antibodies having an Fc region, and Fc fusion proteins. In a preferred embodiment, the antibody is immunoglobulin G (G1 to G4).

The "immunoglobulin G" is a monomeric immunoglobulin composed of 2 γ heavy chains and 2 light chains. As used herein, the term particularly refers to such an immunoglobulin in which a non-native model conformation is generated in the Fc region in stress environments.

As used herein, the "Fc region" refers to an H chain constant region or a partial sequence or partial structure thereof composed of a hinge domain, a CH2 domain, and a CH3 domain. As used herein, the term particularly refers to an Fc region derived from a human antibody.

As used herein, the "Fc region-containing protein" refers to a protein having a sequence or structure of an Fc region in a part of the protein, wherein a non-native conformation is generated in the Fc region in stress environments. The term particularly refers to such an Fc region-containing protein wherein an AF.2A1 polypeptide or an analog thereof used in the method for suppressing formation of an aggregate according to the present invention can recognize and bind to the non-native conformation generated in the Fc region-containing protein.

As used herein, the "non-native conformation" refers to an antibody having no native structure. Specifically, the term refers to a conformational change that occurs in the Fc region when an antibody or an Fc region-containing protein is exposed to stress. Examples of such stress that generates such a non-native conformation include acid treatment, heating, reduction, oxidation, freeze-thawing, physical shocks such as shaking and stirring and the like. In one preferred embodiment, the stress that generates a non-native conformation is an acid treatment, a heat treatment, or a stirring treatment.

The acid treatment means, but is not limited to, exposure to conditions in which pH is preferably equal to or less than 4.0 and more preferably 1.5 to 2.0. For example, immunoglobulin G is reported to form a non-native conformation referred to as the alternatively folded state (AFS), which is different from an usual native conformation, by treatment with a buffer solution of 10 mM Glycine-HCl and 150 mM NaCl, pH 2.0 (Bucher J. et al. (1991), Biochemistry, 30 (28) 6922-6929, Thies M J. et al, (2001), J. Mol. Bio., 309 (5) 1077-1085, Feige M J. et al. (2010), J. Mol. Biol., 399 (5) 719-730).

The denaturation of protein conformation in general is known to be caused by, besides acid treatment, other chemical treatments or physical treatments. Most commonly known is denaturation by heat or that conformation is easily denatured by denaturants such as guanidine hydrochloride (Mechanism of Protein Folding, 2nd edition, R. H. Pain, Springer-Verlag). For example, it has been reported that AFS formation in the Fc region of immunoglobulin G is caused by heat denaturation at around 75 degrees Celsius (Kanmert D. et al. (2011), Chemistry, 50 (6) 981-988). Widely known examples of other chemical treatments and physical treatments include physical shocks such as treatment with a reducing agent, shearing, or stirring. Treatment with a reducing agent here refers to the state in which all or a part of the disulfide bonds in the molecule or between the molecules is cleaved. More specifically, the term refers to the state in which one or disulfide bonds are cleaved by the addition of a reducing agent (such as DTT, β-mercaptoethanol, 2-mercaptoethylamine). In Examples described below, a reduction treatment was provided by treatment with 50 mM 2-mercaptoethylamine for 90 minutes, but such a reagent that produces reduction conditions is not limited to this. The physical shocks such as stirring and shearing are not limited, but it has been reported, for example, that stirring immunoglobulin G solutions at a speed of 700 rpm with a stirring bar causes the oxidation of amino acid residues, denaturation of protein conformation, and protein aggregation thereby (Luo Q. et al. (2011), J. Biol. Chem. 286 (28) 25,134-25,144, Joubert M K. et al. (2012), J. Biol. Chem. 287 (30) 25,266-25,279). In Examples described below, suppression of formation of aggregates is demonstrated using immunoglobulin G in which a non-native conformation is generated by acid treatment. However, the method according to the present invention does not exclude suppression of formation of aggregates due to non-native conformations caused by stress other than acid treatment.

As used herein, the "aggregates" are aggregates formed by aggregation of a plurality of monomers of the antibody or Fc region-containing protein having a non-native conformation due to the non-native conformation. The aggregates also include, for example, small aggregates such as dimers or trimers of the antibody or Fc region-containing protein having a non-native conformation, wherein the aggregates have not able to be removed by conventional filter operations and aggregates larger than such small aggregates. As used herein, the "aggregation precursors" refers to aggregates that have not been able to be removed by conventional filter operations, that is to say, aggregates having particle sizes equal to or less than 220 nm.

As used herein, the "suppression (suppressing)" means reduction of the amount of already existing aggregates or prevention of further formation of aggregates in a solution containing an antibody or an Fc region-containing protein. The reduction of the amount of already existing aggregates or capability of prevention of further formation of aggregates can be evaluated by measuring the particle size in the solution containing the antibody or Fc region-containing protein having a non-native conformation and assessing the presence of aggregates. Specifically, it can be evaluated by, for example, preparing samples by adding or not adding AF.2A1 polypeptide-attached magnetic beads to a solution containing the antibody or Fc region-containing protein having a non-native conformation and comparing the samples on whether the particle size in solution is increased or not after storage for a long period of time.

The "AF.2A1 polypeptide" is known and disclosed, for example, in International Publication No. WO 2014/115229 pamphlet. The "AF.2A1 polypeptide" has been reported to have specific binding activity to Fc regions forming a non-native conformation, as described above. As used herein, the "AF.2A1 polypeptide" has, besides aforementioned activity, binding activity to aggregates containing the antibody or Fc region-containing protein having a non-native conformation. Moreover, the AF.2A1 polypeptide does not bind to native human antibody Fc regions, while having binding activity to aggregates containing the antibody or Fc region-containing protein having a non-native conformation. Therefore, the formation of aggregates in solutions containing the antibody or Fc region-containing protein having a non-native conformation can be suppressed by using the AF.2A1 polypeptide. By using the AF.2A1 polypeptide, it is possible to remove aggregates having particle sizes less than 0.22 μm, in particular, which have been difficult to remove with conventional filter.

In one preferred embodiment, the AF.2A1 polypeptide has binding activity to aggregates caused by human immunoglobulin G containing an Fc region having a non-native conformation.

The AF.2A1 polypeptide can be identified by the amino acid sequence set forth in SEQ ID NO: 1. Moreover, the AF.2A1 polypeptide can be identified by a nucleotide sequence encoding a polypeptide having the amino acid sequence set forth in SEQ ID NO: 1. For example, the AF.2A1 polypeptide consists of a polypeptide encoded by the nucleotide sequence set forth in SEQ ID NO: 2.

The "analog of the AF.2A1 polypeptide" refers to a polypeptide consisting of a polypeptide similar to the AF.2A1 polypeptide and having the same function (that is to say, binding activity to aggregates containing an antibody or an Fc region-containing protein having a non-native conformation) as that of the AF.2A1 polypeptide.

In one embodiment, the analog of the AF.2A1 polypeptide can be identified as a polypeptide consisting of an amino acid sequence modified from the amino acid sequence set forth in SEQ ID NO: 1 by substitution, addition, or deletion of one or several amino acids to an aggregate comprising an antibody or an Fc region-containing protein having a non-native conformation within the range not deteriorating the binding activity. The "several amino acids" refers to, for example, 1 to 8, 1 to 6, preferably 1 to 3, and more preferably one or two amino acids. The number of the amino acid residues in the polypeptide sequence is not limited as long as the polypeptide contains the amino acid sequence set forth in SEQ ID NO: 1 and has the aforementioned binding activity. Specific examples of the analog of the AF.2A1 polypeptide include, for example but are not limited to, those consisting of the amino acid sequences set forth in SEQ ID NOs: 3 to 25.

The AF.2A1 polypeptide or analog thereof may be a recombinant phage or a recombinant virus containing a nucleic acid encoding the AF.2A1 polypeptide or an analog or a transformant containing a vector containing a nucleic acid encoding the AF.2A1 polypeptide or analog thereof. The transformant such as the recombinant phage can be used in the method according to the present invention as long as the transformant displays the aforementioned AF.2A1 polypeptide or analog thereof on its surface and having the binding activity to an aggregate comprising an antibody or an Fc region-containing protein having a non-native conformation.

More specifically, in one embodiment, the AF.2A1 polypeptide or analog thereof consists of:
(A) the amino acid sequence set forth in SEQ ID NO: 1; or
(B) an amino acid sequence modified from the amino acid sequence set forth in SEQ ID NO: 1 by substitution, addition, or deletion of one or several amino acids, wherein the polypeptide consisting of the amino acid sequence exhibits binding activity to an aggregate comprising an antibody or a Fc region-containing protein having a non-native conformation.

The "binding activity to aggregates comprising an antibody or an Fc region-containing protein having a non-native conformation" can be evaluated by whether the formation of aggregates can be suppressed in a solution containing the antibody or Fc region-containing protein having a non-native conformation. Those having the "binding activity to the human antibody Fc region having a non-native conformation" among analogs of the AF.2A1 polypeptide can be presumed to have the binding activity to aggregates comprising an antibody or a Fc region-containing protein having a non-native conformation. The "binding activity to the human antibody Fc region having a non-native conformation" can be evaluated by a known method for measuring binding activity, for example, enzyme-linked immunosorbent assay (ELISA), surface plasmon resonance (SPR), isothermal titration calorimeter (ITC), quartz crystal microbalance (QCM), atomic force microscope (AFM), pull-down assay, electrophoresis, the fluorescence polarization measurement, and the like.

The method for suppressing formation of an aggregate according to the present invention comprises the step of: (i) binding an AF.2A1 polypeptide or an analog thereof in a solution comprising an antibody or an Fc region-containing protein with a monomer and an aggregate derived from the antibody or Fc region-containing protein having a non-native conformation.

In the solution comprising an antibody or an Fc region-containing protein, an antibody or Fc region-containing protein having a non-native conformation and aggregation precursors derived therefrom may be generated due to various stress and these aggregation precursors form larger aggregates latter. In the step (i), an AF.2A1 polypeptide or an analog thereof is bound to a monomer and an aggregate derived from the antibody or Fc region-containing protein having a non-native conformation in the solution. In this step, the AF.2A1 polypeptide or analog thereof binds also to aggregation precursors having a particle size of less than 0.22 μm, which have been difficult to remove with a filter or the like.

A solvent used in binding an AF.2A1 polypeptide or an analog thereof with a monomer and an aggregate derived from the antibody or Fc region-containing protein having a non-native conformation is not particularly limited, as long as the antibody or Fc region-containing protein is dissolved and the binding with the AF.2A1 polypeptide or analog thereof occurs in the solvent. For example, a buffer solution such as PBS and a known solution used in the production of an antibody or a polypeptide may be used. The pH of the solvent is not limited, but preferably in the vicinity of neutral pH.

The conditions such as the temperature and the duration of the binding are also not limited, as long as the AF.2A1 polypeptide or analog thereof can bind to the monomers and aggregates, and a person skilled in the art can perform such binding as appropriate.

In one embodiment, the step (i) is performed by contact between the immobilized AF.2A1 polypeptide or analog thereof and the aggregates.

The immobilized AF.2A1 polypeptide or analog thereof refers to that immobilized onto a solid-phase carrier. Preferred examples of the solid-phase carrier include, but are not limited to, resins such as polystyrene and polyester, biopolymer compounds such as dextran and agarose, and inorganic materials such as metal and glass. The shape of such solid-phase carrier may be any shape such as a particle, a plate, a film, a tip, and a test tube. Immobilization of a polypeptide to those solid-phase carriers can be performed by methods of covalent binding, physical adsorption, ionic binding, intermolecular force. More specific examples include, but are not limited to, immobilization onto particles such as magnetic particles, immobilization onto a filter membrane, immobilization onto a sensor tip of a surface plasmon resonance measuring apparatus by covalent binding, and immobilization onto polymer particles in an affinity chromatography column. Immobilization of the AF.2A1 polypeptide or analog thereof according to the present invention onto a solid-phase carrier allows the AF.2A1 polypeptide or analog thereof to be conveniently used in the removal of aggregates containing an antibody or an Fc region-containing protein having a non-native conformation.

For use in a solution containing an antibody or a Fc region-containing protein in suppressing formation of an aggregate derived from the antibody or Fc region-containing protein having a non-native conformation, the solid-phase carrier is particles (beads) having a particle size of 100 nm to 1 mm, preferably 500 nm to 100 μm, more preferably 1 to 10 μm, and particularly preferably 1 to 5 μm.

The solid-phase carrier is magnetic particles or porous particles made of a polymer resin and preferably magnetic particles. The polymer resin may be any polymer resin, as long as it has on the surface of the substrate a functional group that can bind to protein and examples thereof include agarose, dextran, acrylamide, polyvinyl alcohol, silica, a styrene divinylbenzene copolymer, and polyhydroxymethacrylate.

The AF.2A1 polypeptide or analog thereof can be immobilized onto a solid-phase carrier, for example, via binding of biotin-avidin, biotin-streptavidin, biotin-neutravidin, amino groups, sulfhydryl groups, or the like or by using a bifunctional reagent (such as EMCS, GMBS, HMCS, KUMS). The binding is preferably biotin-avidin, biotin-streptavidin, biotin-neutravidin, amino groups, or sulfhydryl groups, and more preferably biotin-avidin, biotin-streptavidin, or biotin-neutravidin.

The formation of the binding can be assessed, if needed. Examples of the method of assessing the binding include ELISA, SPR, ITC, QCM, AFM, the pull-down assay, electrophoresis, the fluorescence polarization measurement, fluorescence resonance energy transfer (FRET), column chromatography, and immunochromatography.

The method for suppressing formation of aggregates comprises, after step (i), the step of (ii) collecting the monomer and aggregate bound to the polypeptide or analog thereof from the solution.

Examples of means for collection include affinity chromatography, affinity beads, affinity filter, and immunoprecipitation.

Examples of the situation where the application of the method for suppressing formation of an aggregate according to the present invention is preferred include the purification process after antibody production in manufacturing of an antibody, the formulation process in manufacturing of a formulation such as an antibody drug, preparation and administration of a formulation, and the like.

For example, the purification process in manufacturing of an antibody involves low pH conditions and shaking conditions and therefore aggregates may be formed due to these conditions.

In the formulation process in manufacturing of an antibody drug, the antibody that is an active pharmaceutical ingredient is mixed with various additives that serve as a stabilizer, a solubilizing agent, a surfactant, a buffer, isotonizing agent, or a preservative. Due to the chemical effect such as the interaction with these additives, or the physical effect such as solvent exchange, concentration, or dispensing operation, aggregates may be formed. In the preparation and administration, the formation of aggregates due to the storage conditions (such as temperature, humidity, and light) at hospital, aspiration by a syringe, or syringe oil is concerned. Since aggregates may be formed by vibration or temperature during the transportation, aggregates may already be formed when the antibody drug is delivered to a hospital or a drugstore.

By employing the method before those processes illustrated above, not only aggregates that have already formed, but also antibodies having a non-native conformation and aggregate precursors, which are considered to be a cause of formation of aggregates, can be removed.

The method of producing an antibody according to the present invention and the method of producing an antibody drug according to the present invention comprise the method for suppressing formation of an aggregate according to the present invention and suppress the formation of aggregates derived from an antibody or an Fc region-containing protein having a non-native conformation. Therefore, high quality antibodies and antibody drugs whose bioactivity can be maintained for a long period of time can be manufactured by the methods.

The method of preparing an antibody drug and the method of administering an antibody drug according to the present invention make it possible to prepare and administer safe and high quality antibody drugs by suppressing the formation of aggregates.

In another aspect, the present invention also provides an aggregate formation suppressor for suppressing formation of an aggregate in a solution comprising an antibody or an Fc region-containing protein, comprising the AF.2A1 polypeptide or analog thereof.

The AF.2A1 polypeptide or analog thereof contained in the aggregate formation suppressor may be an immobilized AF.2A1 polypeptide or analog thereof, or a recombinant phage or a recombinant virus containing a nucleic acid encoding the AF.2A1 polypeptide or analog thereof or a transformant containing a vector containing a nucleic acid encoding the AF.2A1 polypeptide or analog thereof, as described above.

Hereinafter, the present invention will be described in detail with reference to Examples, but the present invention is not limited by these Example. The contents of Patent Literature and Non-Patent Literature cited herein are incorporated herein by reference.

EXAMPLES

Figure 2:
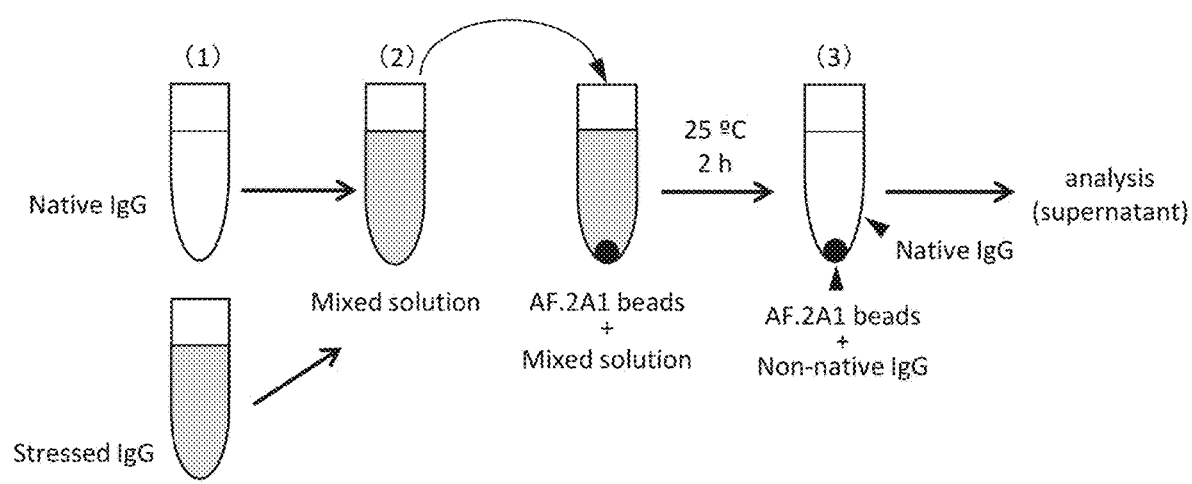
FIG. 2 is an overview diagram illustrating a flow of the process of removing non-native antibodies using AF.2A1 beads from a liquid containing a mixture of a native antibody and non-native antibodies generated by stressing and the process illustrated in FIG. 2 is an embodiment of the "treatment for suppressing formation of aggregates"

Example 1: Suppression of Formation of Aggregates in Solution Containing Mixture of Native Antibody and Non-Native Antibody In order to remove non-native antibodies in antibody drugs, AF.2A1, a small artificial protein having 25 residues capable of recognizing non-native conformations of antibodies was employed. The specific procedure is described below and an overview of the procedure is illustrated in FIG. 2.

Figure 3:
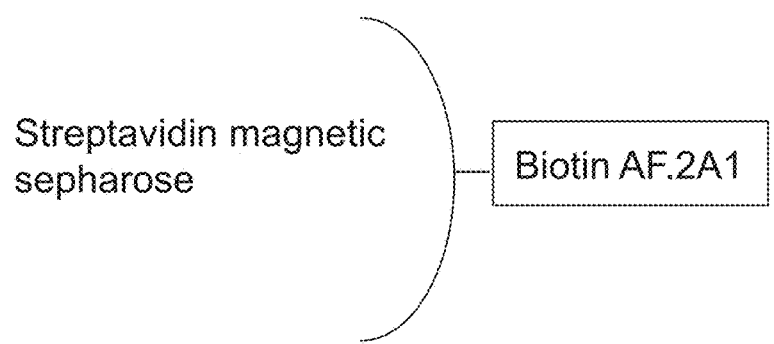
FIG. 3 is a schematic diagram of AF.2A1 beads prepared by binding biotin-labelled AF.2A1 to streptavidin-coated magnetic beads.

The native antibody used was human monoclonal IgG. The native antibody was prepared by diluting in PBS (pH 7.5) to 1 mg/ml and filtering the dilute through a 0.22 µm filter. The acid-stressed antibody was prepared by dialyzing the native antibody solution against an acid buffer at pH 2 (100 mM Glycine-HCl) overnight. This operation causes a non-native conformation in the Fc region in the acid-stressed antibody. The stressed antibodies were neutralized by the addition of a ⅛ volume of 1M Tris-HCl (pH 8) relative to the stressed antibody. After the neutralization, the stressed antibody solution was diluted in PBS (pH 7.5) to a concentration of 1 mg/ml and filtered through a 0.22 µm filter. The 1 mg/ml native antibody and the 1 mg/ml acid-stressed antibody were mixed at a ratio of 9:1 to prepare a mixture solution. Non-native antibodies were then removed by adding AF.2A1 beads to the mixed solution and incubating the resulting mixture at 25° C. for 2 hours. The AF.2A1 beads were prepared by adding 500 µM biotin-labeled AF.2A1 (25 µl) and 1 mg equivalent of streptavidin-coated magnetic beads (Promega Corporation, magnetic particles, 1 µm in diameter) to 1 ml of PBS (pH 7.5) and then allowing the reaction at 25° C. for 30 minutes for the binding (FIG. 3). The mixture was incubated for 2 hours and then only the supernatant fraction containing no AF.2A1 beads was collected to obtain a native antibody fraction.

Example 2: Measurement of Particle Size in Solution after Treatment for Suppressing Aggregate Formation Whether the treatment for suppressing formation of aggregates with AF.2A1 beads can or cannot remove antibody aggregates more effectively than the removal of aggregates using an existing filter was examined. Specifically, the presence or absence of aggregates was examined by the DLS measurement of the particle size in solutions (solutions of (1) to (3) in FIG. 2) before and after the treatment for suppressing formation of aggregates with AF.2A1 beads.

Figure 4A:
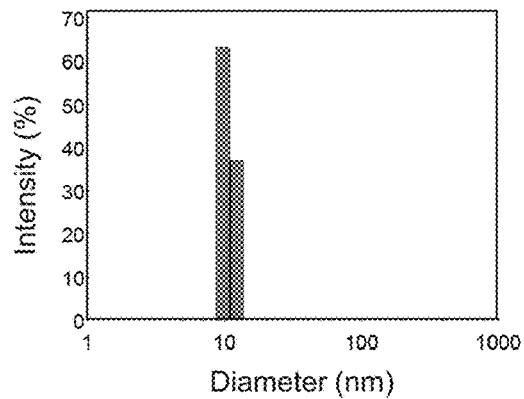
FIG. 4A illustrates the result of measurement of the size of particles by dynamic light scattering in a solution containing only a native antibody.
Figure 4B:
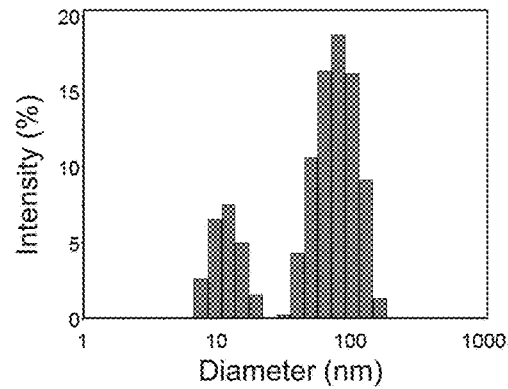
FIG. 4B illustrates the result of measurement of the size of particles by dynamic light scattering in a mixed solution of the native antibody and an acid-stressed antibody.
Figure 4C:
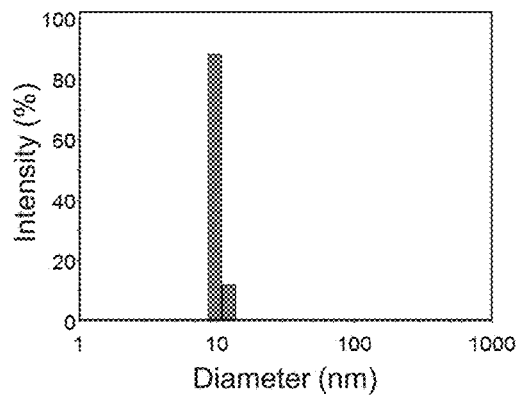
FIG. 4C illustrates the result of measurement of the size of particles by dynamic light scattering in a solution obtained by removing antibody aggregates from the mixed solution of the native antibody and the acid-stressed antibody by using AF.2A1 beads.

The results are illustrated in FIGS. 4A to 4C. FIG. 4A illustrates the result of measurement of the particle size in the solution containing the native antibody (solution of (1) in FIG. 2) and the measurement indicated that the size is 10 nm in diameter. This native antibody and the acid-stressed antibody prepared by the filtration through a 0.22 µm filter were mixed at a ratio of 9:1 and the particle size in the solution (solution of (2) in FIG. 2) was measured by DLS without the treatment for suppressing formation of aggregates with the AF.2A1 beads. The result indicated that various sizes, in addition to 10 nm, of antibody particles were present, revealing that the preparation contains antibody aggregates that was not able to be removed with an existing filter (FIG. 4B). This solution containing antibody aggregates and the AF.2A1 beads were mixed according to the method described in Example 1. It was conformed that after the subsequent treatment for suppressing formation of aggregates (solution of (3) in FIG. 2), the aggregate fraction found in FIG. 4B was removed and only the native antibody was present (FIG. 4C).

The measurement samples were subjected to the removal of aggregates with a 0.22 μm filter before the measurement. However, it was difficult to remove small-size aggregates with the existing filter (FIG. 4B). Therefore, this method newly developed is superior to treatment with the existing filter in that aggregates are exhaustively removed. Moreover, it was indicated that even aggregates that have already been formed in the solution can be removed by using AF.2A1 beads.

Furthermore, the presence or absence of aggregates was examined by analyzing solutions before and after the treatment for suppressing formation of aggregates with AF.2A1 beads by size exclusion chromatography (SEC).

Figure 10:
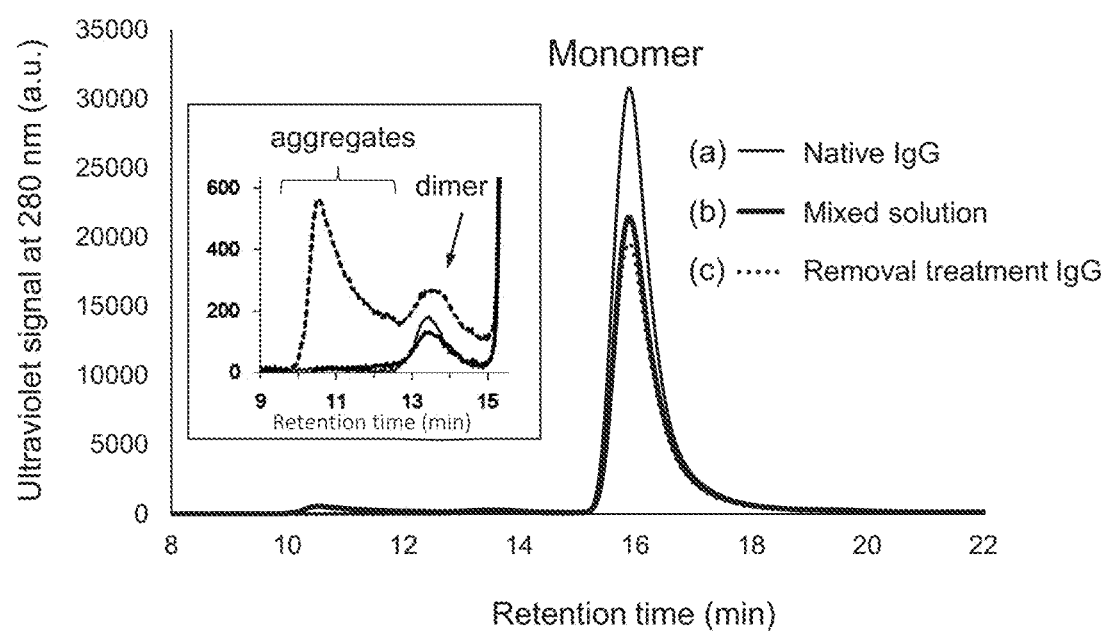
FIG. 10 illustrates the result of size exclusion chromatography analysis of (a) a solution containing only a native antibody, (b) a mixed solution of the native antibody and an acid-stressed antibody, and (c) a solution obtained by removing antibody aggregates from the mixed solution of the native antibody and the acid-stressed antibody by using AF.2A1 beads.

The result is illustrated in FIG. 10. (a) is the result of measurement of the solution containing the native antibody (solution of (1) in FIG. 2), (b) is the result of measurement of the solution obtained by mixing a native antibody and an acid-stressed antibody prepared by filtration through a 0.22 μm filter at a ratio of 7:3 (solution of (2) in FIG. 2), and (c) is the result of measurement of the solution obtained by adding the AF.2A1 beads to the aforementioned acid-stressed antibody mixed solution and subjecting the solution to the treatment for suppressing formation of aggregates (solution of (3) in FIG. 2). While the solution not subjected to the treatment for suppressing formation of aggregates contains dimers and aggregates, the peaks are lowered by the treatment for suppressing the formation. This result indicates that the dimers are removed and this confirms that this technique is capable of exhaustively removing aggregates regardless of their sizes.

Example 3: Examination of Amount of Aggregate that can be Removed with AF.2A1 Beads How much aggregates in solutions containing a native antibody and a non-native antibody can be removed with AF.2A1 beads was examined.

Figure 5:
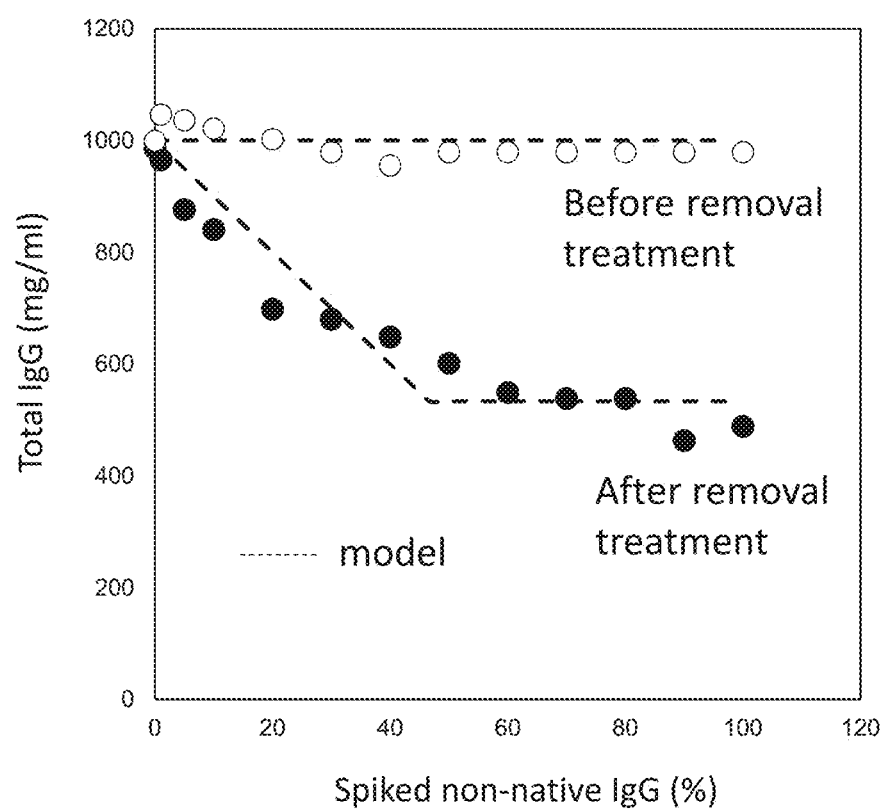
FIG. 5 is a graph illustrating the result of measurement of the antibody concentration before and after the treatment for suppressing formation of aggregates with AF.2A1 beads in solutions obtained by mixing a native antibody and a stressed antibody at a variety of ratios (0 to 100% stressed antibody), in which the open circles and the filled circles respectively indicate the concentrations of the antibody in the soluble fraction before and after the treatment. The dashed line indicates the antibody concentration in calculation.

Specifically, the 1 mg/ml native antibody and the 1 mg/ml acid-stressed antibody prepared in Example 1 were mixed at various ratios (0 to 100% acid-stressed antibody). Subsequently, the treatment for suppressing formation of aggregates in the solution with AF.2A1 beads was performed in the same manner as that in Example 1. The antibodies before and after the treatment were centrifuged at 500×g for 1 minute and the antibody concentration of the soluble fraction was measured. The higher the ratio of the acid-stressed antibody in the mixture was, the more aggregates were removed and the lower the antibody concentration the mixed solution was, as a result. As illustrated in FIG. 5, aggregates containing 470 ug equivalent of non-native antibody was removed with 1 mg equivalent of AF.2A1 beads.

Example 4: Differences of Antibody Aggregate Formation Between in Presence and Absence of Treatment for Suppressing Formation of Aggregates Non-native antibody generated by stress has been reported to change into aggregates larger in size over time. Therefore, the aggregate formation during the stationary incubation at 25° C. with or without the treatment for suppressing formation of aggregates with AF.2A1 beads after mixing a native antibody and an acid-stressed antibody was examined.

Specifically, the examination was conducted as follows. The native antibody and the stressed antibody were prepared in the same manner as that in Example 1 above. The 1 mg/ml native antibody and the 1 mg/ml acid-stressed antibody at a ratio of 0, 1, 5, 10, or 20% were mixed to prepare a mixture. Immediately after the mixing, suppression of formation of aggregates in the solutions with AF.2A1 beads was performed in the same manner as that in Example 1. The mixtures before and after the treatment with AF.2A1 beads were centrifuged at 500×g for 1 minute. Subsequently, the supernatants were left to stand at 25° C. for 0, 3, 7, 21, 34, 48, 63 days and the antibody concentration of the soluble fraction was measured. For the measurement of antibody concentration, the antibody concentration was determined by measuring the absorbance at 280 nm with NanoPhotometer from Implen Inc. FIGS. 6A and 6B illustrate the result of the measurement of the antibody concentration only in the soluble fraction obtained after spinning-down. Without the treatment with AF.2A1 beads, the antibody aggregates and precipitates in a time-dependent manner and the total antibody concentration was decreased (FIG. 6A). With the treatment for suppressing formation of aggregates with AF.2A1 beads, the time-dependent aggregate formation was markedly suppressed (FIG. 6B). Therefore, the removal of small aggregates that have not been possible to remove in the existing technology by this technology of suppressing aggregation formation makes it possible to store antibodies stably for a long period of time.

Example 5 this Technology of Suppressing Aggregation Formation is Commonly Available for Plurality of Antibodies In order to examine whether this technique is available for plurality of antibodies but not only one antibody, the examination using 3 therapeutic monoclonal antibodies (mAb1, mAb2, mAb3) and 1 polyclonal antibody (pAb) was conducted. For each antibody, a native antibody and an acid-stressed antibody were prepared in the same manner as that in Example 1. The 1 mg/ml native antibody and the 1 mg/ml acid-stressed antibody at a ratio of 5% were mixed and then the treatment for suppressing formation of aggregates with AF.2A1 beads was performed in the same manner as that in Example 1. Subsequently, the mixtures were left to stand at 25° C. for 0, 3, 7, 10, 14 days and the particle size in the solutions was measured by DLS.

Figure 7A:
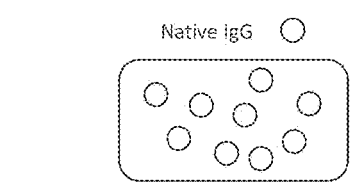
FIG. 7A is an outlook chart of particles in a solution containing only a native antibody.
Figure 7B:
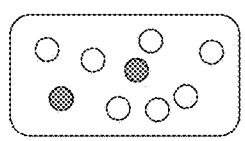
FIG. 7B is an outlook chart of particles in a solution obtained by mixing a native antibody and stressed antibody.
Figure 7C:
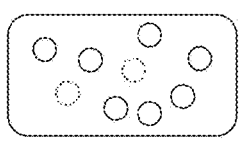
FIG. 7C is an outlook chart of particles in a solution obtained by mixing a native antibody and stressed antibody and then subjecting the mixture to a treatment for suppressing formation of aggregates.
Figure 7D:
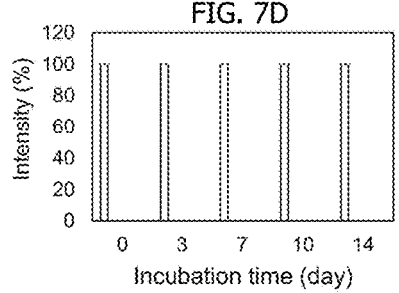
FIG. 7D is a graph illustrating the particle size when only a native antibody is left to stand using a therapeutic monoclonal antibody (mAb1)
Figure 7E:
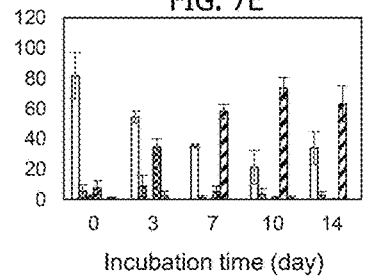
FIG. 7E is a graph illustrating the particle size when a native antibody and stressed antibody were mixed and them the mixture was left to stand without AF.2A1 beads treatment using a therapeutic monoclonal antibody (mAb1)
Figure 7F:
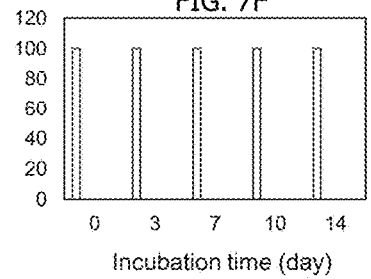
FIG. 7F is a graph illustrating the particle size when a native antibody and stressed antibody were mixed and then the mixture was subjected to a treatment for suppressing formation of aggregates with AF.2A1 beads and left to stand using a therapeutic monoclonal antibody (mAb1)
Figure 7G:
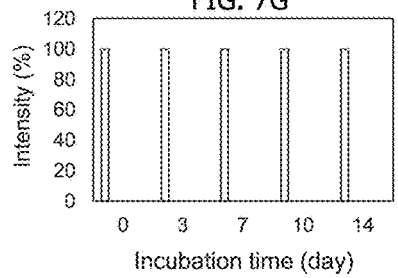
FIG. 7G is a graph illustrating the particle size when only a native antibody is left to stand using a therapeutic monoclonal antibody (mAb2)
Figure 7H:
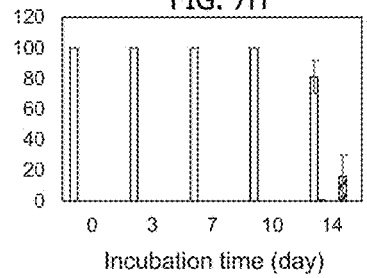
FIG. 7H is a graph illustrating the particle size when a native antibody and stressed antibody were mixed and them the mixture was left to stand without AF.2A1 beads treatment using a therapeutic monoclonal antibody (mAb2)
Figure 7I:
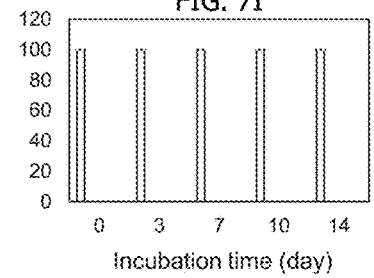
FIG. 7I is a graph illustrating the particle size when a native antibody and stressed antibody were mixed and then the mixture was subjected to a treatment for suppressing formation of aggregates with AF.2A1 beads and left to stand using a therapeutic monoclonal antibody (mAb2)
Figure 7J:
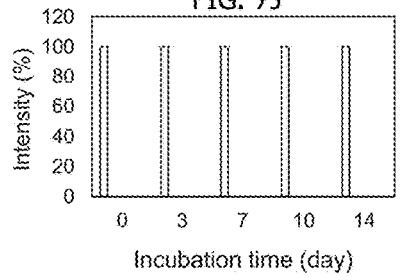
FIG. 7J is a graph illustrating the particle size when only a native antibody is left to stand using a therapeutic monoclonal antibody (mAb3)
Figure 7K:
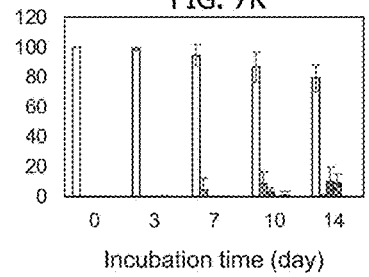
FIG. 7K is a graph illustrating the particle size when a native antibody and stressed antibody were mixed and them the mixture was left to stand without AF.2A1 beads treatment using a therapeutic monoclonal antibody (mAb3)
Figure 7L:
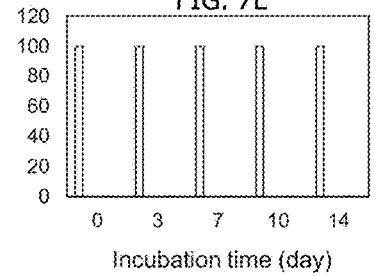
FIG. 7L is a graph illustrating the particle size when a native antibody and stressed antibody were mixed and then the mixture was subjected to a treatment for suppressing formation of aggregates with AF.2A1 beads and left to stand using a therapeutic monoclonal antibody (mAb3)
Figure 7M:
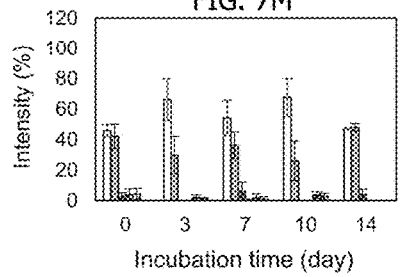
FIG. 7M is a graph illustrating the particle size when only a native antibody is left to stand using a polyclonal antibody (pAb)
Figure 7N:
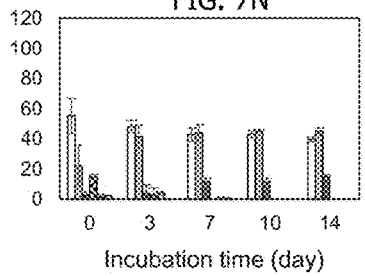
FIG. 7N is a graph illustrating the particle size when a native antibody and stressed antibody were mixed and them the mixture was left to stand without AF.2A1 beads treatment using a polyclonal antibody (pAb)
Figure 7O:
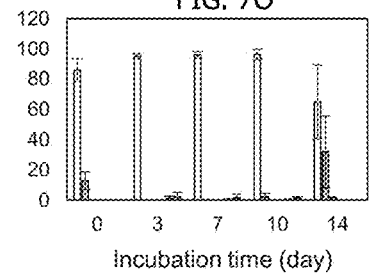
FIG. 7O is a graph illustrating the particle size when a native antibody and stressed antibody were mixed and then the mixture was subjected to a treatment for suppressing formation of aggregates with AF.2A1 beads and left to stand using a polyclonal antibody (pAb).
Figure 8A:
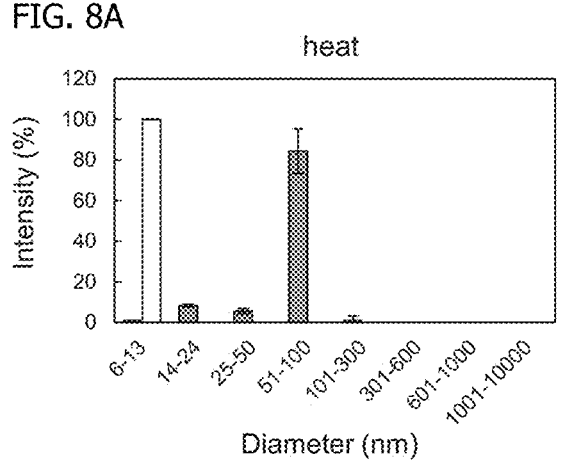
FIGS. 8A to 8F are graphs illustrating the result of DLS measurement of the antibody size in a solution obtained by applying heat stress (FIG. 8A), freeze-thawing stress (FIG. 8B), stirring stress (FIG. 8C), reduction stress (FIG. 8D), and acid stress (pH 3.
Figure 8B:
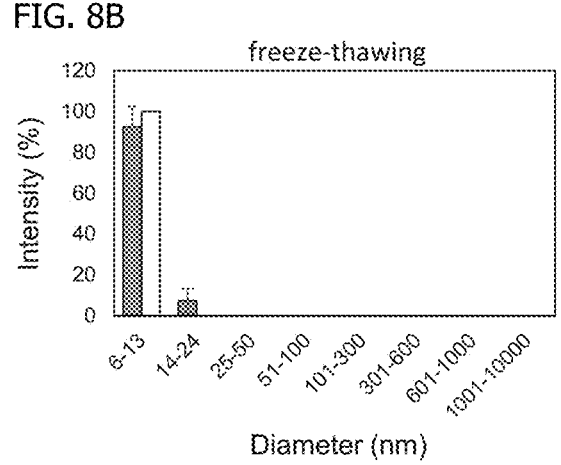
Figure 8C:
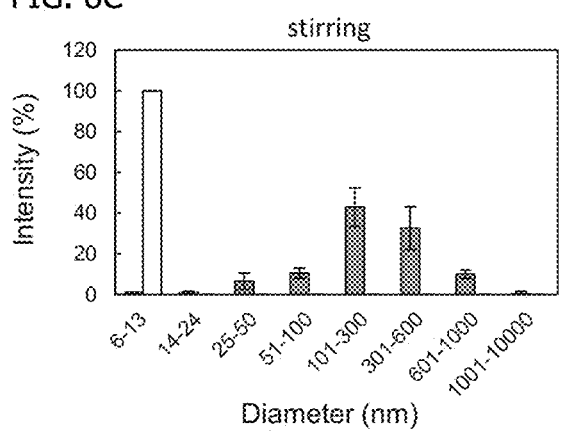
Figure 8D:
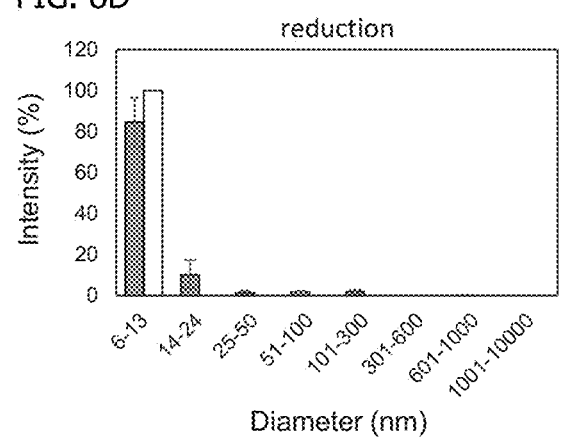
Figure 8E:
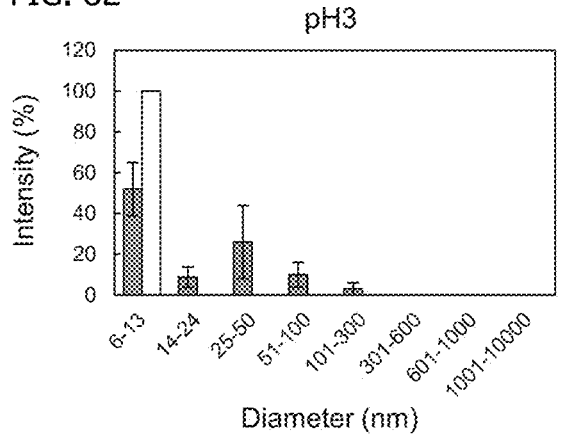
Figure 8F:
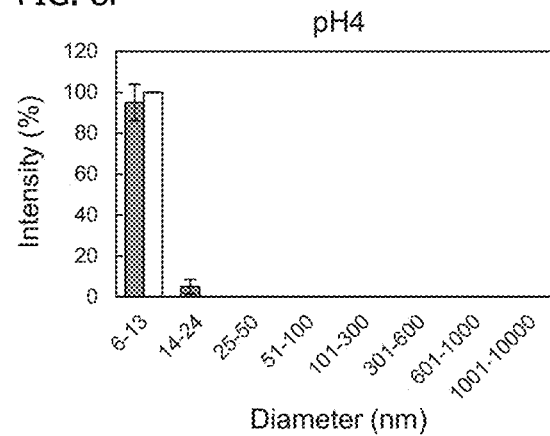

The results indicated that removal of aggregates in the beginning can markedly suppress the latter formation of aggregates for all the antibodies examined (comparison of FIGS. 7E, 7H, 7K, and 7N and FIGS. 7F, 7I, 7L and 7O). As for the monoclonal antibodies, while the formation of large aggregates over time was observed without the treatment for suppressing formation of aggregates after mixing the native antibody and the acid-stressed antibody (FIGS. 7E, 7H, and 7K), no aggregate formation was observed even two weeks later in the sample from which non-native antibodies and aggregates derived therefrom were removed with AF.2A1 beads, as in the sample containing only the native antibody (FIGS. 7F, 7I, and 7L). As for the polyclonal antibody, it was found that fractions of various sizes were contained even without mixing the acid-stressed antibody (FIG. 7M). However, it was demonstrated that polyclonal antibodies having smaller contents of impurities can be obtained by having the removal treatment with AF.2A1 beads (FIG. 7O).] It was suggested that this technique is available, not only in quality control of antibody drugs, but also for suppressing aggregate formation and maintaining the purity of antibodies to be used as a study reagent.

Example 6: Possible to Remove Non-Native Monomers, which Cannot Detect with Existing Analytical Instrument In the results of FIGS. 7H and 7K, aggregates were not detected by DLS on Day 0 in the samples obtained without treating the mixture of a native antibody and an acid-stressed antibody with beads. However, the aggregate fraction in small amounts were observed from one week later and formation of larger aggregates was increased by the longer period of time of standing (FIGS. 7H and 7K). On the contrast, in the samples obtained with the treatment of the mixture of a native antibody and an acid-stressed antibody with beads, aggregates were not formed even two weeks later. The all 3 samples: the one containing only the native antibody, the one obtained without the treatment of the mixture of the native antibody and the acid-stressed antibody with beads, and the one obtained with the treatment of the mixture of the native antibody and the acid-stressed antibody with beads contain no small aggregates on Day 0, but aggregates were formed in a time-dependent manner only in those samples obtained without the treatment with beads. This result indicates that such samples contained non-native monomers.

The foregoing results revealed that the non-native monomers that are difficult to detect with existing apparatuses and the small aggregates that cannot be removed by existing techniques are "aggregation precursors" and that suppression of aggregate formation for a long time is possible by applying this technology of suppressing formation of aggregates to these aggregation precursors, which can become larger aggregates latter.

Example 7: Suppression of Formation of Aggregates Containing Non-Native Antibody Formed by Various Stress As illustrated in FIGS. 8A-8F, a native antibody is diluted in PBS (pH 7.5) to a concentration of 1 mg/ml and then subjected to one of the following stress treatments: heat stress (50° C. for 10 hours)(FIG. 8A), freeze-thawing stress (freezing at −80° C. for 15 min and thawing at room temperature for 15 min (repeated 10 times)(FIG. 8B), stirring stress (200 rpm for 5 hours)(FIG. 8C), reduction stress (in 50 mM 2-ME at 37° C. for 90 min)(FIG. 8D), or acid stress (at pH 3 (FIG. 8E) and pH 4 (FIG. 8F) each for 16 hours). Subsequently, the treatment for suppressing formation of aggregates with AF.2A1 beads was performed in the same manner as that in Example 1 and the particle size in the solutions was measured by DLS. The white and gray bars respectively indicate the results of the measurement with or without the treatment for suppressing formation of aggregates with AF.2A1 beads. (A) illustrates the result of the heat stress, (B) illustrates the result of the freeze-thawing stress, (C) illustrates the result of the stirring stress, (D) illustrates the result of the reduction stress, (E) illustrates the result of the acid stress at pH 3, and (F) illustrates the acid stress at pH 4. The formation of aggregates was observed with any of the stresses. With the treatment for suppressing formation of aggregates with AF.2A1 beads, the aggregate formation was markedly suppressed.

From the foregoing results, it is considered that the technology of suppressing formation of aggregates using the AF.2A1 peptide is also effective for aggregates generated by stresses other than acid.

Example 8: Aggregates Formed by Long-Term Storage of Highly Purified Native Antibody can be Suppressed The suppressing effect of removing non-native antibodies generated by various stress and aggregate caused thereby on later-formed aggregates had been examined. It was then examined whether it is also effective on the suppression of formation of aggregates generated during the stationary incubation of an antibody, prepared by mimicking the actual manufacturing process of antibody drugs, at 4° C., 25° C., 37° C. without stressing.

Specifically, 1 mg/ml monoclonal antibodies (mAb4, mAb5) were treated with AF.2A1 beads in the same manner as that in Example 1 and incubated stationary at a temperature of 4° C., 25° C., or 37° C. The particle size in the solutions were measured by DLS on Day 0 (A), Day 14 (B), a month later (C), 3 months later (D), and 6 months later (E).

The result is illustrated in FIGS. 9A to 9E. Without the treatment for suppressing formation of aggregates with AF.2A1 beads (upper graphs in FIGS. 9A to 9E), the formation of aggregates was observed even with highly purified antibody after the long term-storage at 25° C. and 37° C. With the treatment for suppressing formation of aggregates with AF.2A1 beads (lower graphs in FIGS. 9A to 9E), the formation of aggregates was markedly suppressed.

The foregoing results indicate that the technology of suppressing formation of aggregates using the AF.2A1 peptide can make the long-term stable storage possible by removing aggregation precursors, which can become larger aggregates later.

All publications, patents, and patent applications cited herein are incorporated herein by reference as they are.

SEQUENCE LISTING FREE TEXT

SEQ ID NO: 1: Chemical synthesis
SEQ ID NO: 2: Chemical synthesis
SEQ ID NO: 3: Chemical synthesis
SEQ ID NO: 4: Chemical synthesis
SEQ ID NO: 5: Chemical synthesis
SEQ ID NO: 6: Chemical synthesis
SEQ ID NO: 7: Chemical synthesis
SEQ ID NO: 8: Chemical synthesis
SEQ ID NO: 9: Chemical synthesis
SEQ ID NO: 10: Chemical synthesis
SEQ ID NO: 11: Chemical synthesis
SEQ ID NO: 12: Chemical synthesis
SEQ ID NO: 13: Chemical synthesis
SEQ ID NO: 14: Chemical synthesis
SEQ ID NO: 15: Chemical synthesis
SEQ ID NO: 16: Chemical synthesis
SEQ ID NO: 17: Chemical synthesis
SEQ ID NO: 18: Chemical synthesis
SEQ ID NO: 19: Chemical synthesis
SEQ ID NO: 20: Chemical synthesis
SEQ ID NO: 21: Chemical synthesis
SEQ ID NO: 22: Chemical synthesis
SEQ ID NO: 23: Chemical synthesis
SEQ ID NO: 24: Chemical synthesis
SEQ ID NO: 25: Chemical synthesis

[Sequence Listing]

What is claimed is:

1. A method for suppressing, in a solution comprising an antibody or an Fc region-containing protein, formation of an aggregate derived from an antibody or an Fc region-containing protein having a non-native conformation, the method comprising:

the steps of
(i) binding an AF.2A1 polypeptide or an analog thereof with a monomer having a non-native conformation and an aggregate derived from the antibody or Fc region-containing protein having a non-native conformation in the solution; and
(ii) collecting the monomer having a non-native conformation and aggregate bound to the polypeptide or analog thereof from the solution, wherein
the AF.2A1 polypeptide comprises the amino acid sequence of SEQ ID NO: 1 and the analog thereof comprises the amino acid sequence selected from the group consisting of SEQ ID NOs: 3 to 25,
the antibody or the Fc region-containing protein is a human immunoglobulin G (IgG) or a human IgG-containing protein, and
the aggregate comprises an aggregate precursor having a particle size less than 0.22 µm.

2. The method according to claim 1, wherein the non-native conformation is caused by stress selected from the group consisting of acid treatment, heating, reduction, oxidization, freeze-thawing, and a physical stimulation.

3. The method according to claim 1, wherein the antibody is any of human immunoglobulin G1 to 4.

4. The method according to claim 1, wherein the AF.2A1 polypeptide or analog thereof is immobilized onto a solid-phase carrier.

5. The method according to claim 4, wherein the solid-phase carrier is a particle having a particle size of 1 to 10 µm.

6. The method according to claim 4, wherein the solid-phase carrier is a magnetic particle or a porous particle made of a polymer resin.

7. The method according to claim 4, wherein the AF.2A1 polypeptide or analog is immobilized onto a solid-phase carrier via any binding selected from the group consisting of biotin-avidin, biotin-streptavidin, and biotin-neutravidin.

8. A method of producing an antibody, comprising the method for suppressing formation of an aggregate derived from an antibody or an Fc region-containing protein having a non-native conformation according to claim 1.

9. A method of producing an antibody drug, comprising the method for suppressing formation of an aggregate derived from an antibody or an Fc region-containing protein having a non-native conformation according to claim 1.

* * * * *

SEQUENCE LISTING

<160> NUMBER OF SEQ ID NOS: 25

<210> SEQ ID NO 1
<211> LENGTH: 25
<212> TYPE: PRT
<213> ORGANISM: Artificial Sequence
<220> FEATURE:
<223> OTHER INFORMATION: Chemically synthesized

<400> SEQUENCE: 1

Gly Val Val Arg Gln Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 2
<211> LENGTH: 75
<212> TYPE: DNA
<213> ORGANISM: Artificial Sequence
<220> FEATURE:
<223> OTHER INFORMATION: Chemically synthesized

<400> SEQUENCE: 2
ggagtagtac gacaatggtc aggttatgat cctcgtaccg gtacctggcg ttcctccata      60
gcttatggtg gtggt                                                      75

<210> SEQ ID NO 3
<211> LENGTH: 17
<212> TYPE: PRT
<213> ORGANISM: Artificial Sequence
<220> FEATURE:
<223> OTHER INFORMATION: Chemically synthesized

<400> SEQUENCE: 3

Tyr Asp Pro Arg Thr Gly Thr Trp Arg Ser Ser Ile Ala Tyr Gly Gly
1               5                   10                  15

Gly

<210> SEQ ID NO 4
<211> LENGTH: 25
<212> TYPE: PRT
<213> ORGANISM: Artificial Sequence
<220> FEATURE:
<223> OTHER INFORMATION: Chemically synthesized

<400> SEQUENCE: 4

Ala Gly Ser Arg Arg Ala His Gly Tyr Asp Pro Arg Thr Gly Thr Trp
1               5                   10                  15

Arg Ser Ser Ile Ala Tyr Gly Gly Gly
            20                  25

<210> SEQ ID NO 5
<211> LENGTH: 25
<212> TYPE: PRT
<213> ORGANISM: Artificial Sequence
<220> FEATURE:
<223> OTHER INFORMATION: Chemically synthesized -continued

```
<400> SEQUENCE: 5

Ala Ser Val Arg Ser Trp Ser Ser Tyr Asp Pro Arg Thr Gly Thr Trp
1               5                   10                  15

Arg Ser Ser Ile Ala Tyr Gly Gly Gly
            20                  25

<210> SEQ ID NO 6
<211> LENGTH: 25
<212> TYPE: PRT
<213> ORGANISM: Artificial Sequence
<220> FEATURE:
<223> OTHER INFORMATION: Chemically synthesized

<400> SEQUENCE: 6

Ser Trp Arg Arg Arg Gly Ser Ser Tyr Asp Pro Arg Thr Gly Thr Trp
1               5                   10                  15

Arg Ser Ser Ile Ala Tyr Gly Gly Gly
            20                  25

<210> SEQ ID NO 7
<211> LENGTH: 25
<212> TYPE: PRT
<213> ORGANISM: Artificial Sequence
<220> FEATURE:
<223> OTHER INFORMATION: Chemically synthesized

<400> SEQUENCE: 7

Thr Gly Arg Gly Arg Ser Ala Arg Tyr Asp Pro Arg Thr Gly Thr Trp
1               5                   10                  15

Arg Ser Ser Ile Ala Tyr Gly Gly Gly
            20                  25

<210> SEQ ID NO 8
<211> LENGTH: 25
<212> TYPE: PRT
<213> ORGANISM: Artificial Sequence
<220> FEATURE:
<223> OTHER INFORMATION: Chemically synthesized

<400> SEQUENCE: 8

His Trp Val Asn Gly Arg Ser Gly Tyr Asp Pro Arg Thr Gly Thr Trp
1               5                   10                  15

Arg Ser Ser Ile Ala Tyr Gly Gly Gly
            20                  25

<210> SEQ ID NO 9
<211> LENGTH: 25
<212> TYPE: PRT
<213> ORGANISM: Artificial Sequence
<220> FEATURE:
<223> OTHER INFORMATION: Chemically synthesized

<400> SEQUENCE: 9

Glu Arg Trp Ile Thr Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 10
<211> LENGTH: 25
<212> TYPE: PRT
<213> ORGANISM: Artificial Sequence
<220> FEATURE:
<223> OTHER INFORMATION: Chemically synthesized
```

```
<400> SEQUENCE: 10

Gly Ser Val Val Arg Trp Arg Gly Tyr Asp Pro Arg Thr Gly Thr Trp
1               5                   10                  15

Arg Ser Ser Ile Ala Tyr Gly Gly Gly
            20                  25

<210> SEQ ID NO 11
<211> LENGTH: 25
<212> TYPE: PRT
<213> ORGANISM: Artificial Sequence
<220> FEATURE:
<223> OTHER INFORMATION: Chemically synthesized

<400> SEQUENCE: 11

Gly Val Val Arg Arg Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 12
<211> LENGTH: 26
<212> TYPE: PRT
<213> ORGANISM: Artificial Sequence
<220> FEATURE:
<223> OTHER INFORMATION: Chemically synthesized

<400> SEQUENCE: 12

Gly Val Val Arg Gln Ala Gln Ser Gly Tyr Asp Pro Arg Thr Gly Thr
1               5                   10                  15

Trp Arg Ser Ser Ile Ala Tyr Gly Gly Gly
            20                  25

<210> SEQ ID NO 13
<211> LENGTH: 24
<212> TYPE: PRT
<213> ORGANISM: Artificial Sequence
<220> FEATURE:
<223> OTHER INFORMATION: Chemically synthesized

<400> SEQUENCE: 13

Gly Val Val Arg Gln Trp Ser Gly Tyr Asp Pro Arg Thr Gly Thr Trp
1               5                   10                  15

Ala Ser Ser Ile Ala Tyr Gly Gly
            20

<210> SEQ ID NO 14
<211> LENGTH: 25
<212> TYPE: PRT
<213> ORGANISM: Artificial Sequence
<220> FEATURE:
<223> OTHER INFORMATION: Chemically synthesized

<400> SEQUENCE: 14

Gly Val Val Arg Gln Trp Ser Gly Tyr Asp Pro Arg Thr Gly Thr Trp
1               5                   10                  15

Arg Ala Ser Ile Ala Tyr Gly Gly Gly
            20                  25

<210> SEQ ID NO 15
<211> LENGTH: 25
<212> TYPE: PRT
<213> ORGANISM: Artificial Sequence
<220> FEATURE:
<223> OTHER INFORMATION: Chemically synthesized
```

```
<400> SEQUENCE: 15

Gly Val Val Arg Gln Trp Ser Gly Tyr Asp Pro Arg Thr Gly Thr Trp
1               5                   10                  15

Arg Ser Ala Ile Ala Tyr Gly Gly Gly
            20                  25

<210> SEQ ID NO 16
<211> LENGTH: 25
<212> TYPE: PRT
<213> ORGANISM: Artificial Sequence
<220> FEATURE:
<223> OTHER INFORMATION: Chemically synthesized

<400> SEQUENCE: 16

Gly Val Val Arg Gln Trp Ser Gly Tyr Asp Pro Arg Thr Gly Thr Trp
1               5                   10                  15

Arg Ser Ser Ala Ala Tyr Gly Gly Gly
            20                  25

<210> SEQ ID NO 17
<211> LENGTH: 25
<212> TYPE: PRT
<213> ORGANISM: Artificial Sequence
<220> FEATURE:
<223> OTHER INFORMATION: Chemically synthesized

<400> SEQUENCE: 17

Gly Ala Val Tyr Arg Arg Ser Phe Tyr Asp Pro Arg Thr Gly Thr Trp
1               5                   10                  15

Arg Ser Ser Ile Ala Tyr Arg Gly Gly
            20                  25

<210> SEQ ID NO 18
<211> LENGTH: 25
<212> TYPE: PRT
<213> ORGANISM: Artificial Sequence
<220> FEATURE:
<223> OTHER INFORMATION: Chemically synthesized

<400> SEQUENCE: 18

Gly Val Val Arg Arg Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 19
<211> LENGTH: 26
<212> TYPE: PRT
<213> ORGANISM: Artificial Sequence
<220> FEATURE:
<223> OTHER INFORMATION: Chemically synthesized

<400> SEQUENCE: 19

Gly Val Val Arg Gln Ala Gln Ser Gly Tyr Asp Pro Arg Thr Gly Thr
1               5                   10                  15

Trp Arg Ser Ser Ile Ala Tyr Gly Gly Gly
            20                  25

<210> SEQ ID NO 20
<211> LENGTH: 25
<212> TYPE: PRT
<213> ORGANISM: Artificial Sequence
<220> FEATURE:
<223> OTHER INFORMATION: Chemically synthesized
```

```
<400> SEQUENCE: 20

Gly Val Val Arg Gln Trp Ala Gly Tyr Asp Pro Arg Thr Gly Thr Trp
1               5                   10                  15

Arg Ser Ser Ile Ala Tyr Gly Gly Gly
            20                  25

<210> SEQ ID NO 21
<211> LENGTH: 25
<212> TYPE: PRT
<213> ORGANISM: Artificial Sequence
<220> FEATURE:
<223> OTHER INFORMATION: Chemically synthesized

<400> SEQUENCE: 21

Gly Val Val Arg Gln Trp Ser Gly Tyr Asp Pro Arg Thr Gly Thr Trp
1               5                   10                  15

Ala Ser Ser Ile Ala Tyr Gly Gly Gly
            20                  25

<210> SEQ ID NO 22
<211> LENGTH: 25
<212> TYPE: PRT
<213> ORGANISM: Artificial Sequence
<220> FEATURE:
<223> OTHER INFORMATION: Chemically synthesized

<400> SEQUENCE: 22

Gly Val Val Arg Gln Trp Ser Gly Tyr Asp Pro Arg Thr Gly Thr Trp
1               5                   10                  15

Arg Ala Ser Ile Ala Tyr Gly Gly Gly
            20                  25

<210> SEQ ID NO 23
<211> LENGTH: 25
<212> TYPE: PRT
<213> ORGANISM: Artificial Sequence
<220> FEATURE:
<223> OTHER INFORMATION: Chemically synthesized

<400> SEQUENCE: 23

Gly Val Val Arg Gln Trp Ser Gly Tyr Asp Pro Arg Thr Gly Thr Trp
1               5                   10                  15

Arg Ser Ala Ile Ala Tyr Gly Gly Gly
            20                  25

<210> SEQ ID NO 24
<211> LENGTH: 25
<212> TYPE: PRT
<213> ORGANISM: Artificial Sequence
<220> FEATURE:
<223> OTHER INFORMATION: Chemically synthesized

<400> SEQUENCE: 24

Gly Val Val Arg Gln Trp Ser Gly Tyr Asp Pro Arg Thr Gly Thr Trp
1               5                   10                  15

Arg Ser Ser Ala Ala Tyr Gly Gly Gly
            20                  25

<210> SEQ ID NO 25
<211> LENGTH: 25
<212> TYPE: PRT
<213> ORGANISM: Artificial Sequence
<220> FEATURE:
<223> OTHER INFORMATION: Chemically synthesized
```

```
<400> SEQUENCE: 25

Gly Val Val Arg Gln Trp Ser Gly Gly Gly Ser Gly Gly Gly
1               5                   10                  15

Arg Ser Ser Ile Ala Tyr Gly Gly Gly
                20                  25
```